United States Patent
Bhambure et al.

(10) Patent No.: US 12,371,482 B2
(45) Date of Patent: Jul. 29, 2025

(54) CLONING AND EXPRESSION OF IN VIVO REFOLDED ANTIBODY FRAGMENT

(71) Applicant: COUNCIL OF SCIENTIFIC & INDUSTRIAL RESEARCH, New Delhi (IN)

(72) Inventors: Rahul Sharad Bhambure, Pune (IN); Aatir Asad Tungekar, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 972 days.

(21) Appl. No.: 17/600,867

(22) PCT Filed: Apr. 1, 2020

(86) PCT No.: PCT/IN2020/050312
§ 371 (c)(1),
(2) Date: Oct. 1, 2021

(87) PCT Pub. No.: WO2020/202208
PCT Pub. Date: Oct. 8, 2020

(65) Prior Publication Data
US 2022/0177562 A1 Jun. 9, 2022

(30) Foreign Application Priority Data
Apr. 2, 2019 (IN) .............................. 201911013248

(51) Int. Cl.
*C07K 16/22* (2006.01)
*C12N 15/70* (2006.01)

(52) U.S. Cl.
CPC .............. *C07K 16/22* (2013.01); *C12N 15/70* (2013.01); *C07K 2317/14* (2013.01)

(58) Field of Classification Search
CPC ..... C07K 16/22; C07K 2317/14; C12N 15/70
See application file for complete search history.

(56) References Cited

U.S. PATENT DOCUMENTS

| | | | |
|---|---|---|---|
| 2013/0197200 A1* | 8/2013 | Bian ................. | B01D 15/363 530/416 |
| 2017/0159060 A1* | 6/2017 | Salunkhe ............ | C07K 14/605 |

FOREIGN PATENT DOCUMENTS

| | | |
|---|---|---|
| WO | WO 2018/173075 | 9/2018 |
| WO | WO 2018/211529 | 11/2018 |

OTHER PUBLICATIONS

Moreno (European Journal of Pharmaceutics and Biopharmaceutics 108 (2016): 156-167) (Year: 2016).*
Weikart (Microbiology 143.5 (1997): 1567-1574) (Year: 1997).*
Martinez (Trends in biotechnology 37.3 (2019): 237-241) (Year: 2019).*
Larentis (BMC research notes 7 (2014): 1-13) (Year: 2014).*
Qoronfleh (Applied biochemistry and biotechnology 80 (1999): 107-120) (Year: 1999).*
Campani (Bioprocess and biosystems engineering 40 (2017): 1621-1633) (Year: 2017).*
Adnan (Renewable energy 66 (2014): 625-633) (Year: 2014).*
Fathi-Roudsari M. et al. Comparison of Three *Escherichia coli* Strains in Recombinant Production of Reteplase. *Avicenna J Med Biotechnol.* 2016;8(1):16-22.
Gaciarz, A., et al. Systematic screening of soluble expression of antibody fragments in the cytoplasm of *E. coli*. *Microb Cell Fact* 15, 22 (2016). https://doi.org/10.1186/s12934-016-0419-5.
Indian Patent Application No. 201711017654 filed May 19, 2017 in 30 pages.
Indian Patent Application No. 201711010410 filed Mar. 24, 2017 in 40 pages.
Kong B., Guo G.L. (2014) Soluble Expression of Disulfide Bond Containing Proteins FGF15 and FGF19 in the Cytoplasm of *Escherichia coli*. PLOS One 9(1): e85890. https://doi.org/10.1371/journal.pone.0085890.

* cited by examiner

*Primary Examiner* — Anne M. Gussow
*Assistant Examiner* — Kyle T Rega
(74) *Attorney, Agent, or Firm* — Norton Rose Fulbright US LLP

(57) ABSTRACT

The present invention relates to a process for production and recovery of in-vivo refolded recombinant antibody fragment in a soluble form in the cytoplasm of a microbial expression system. More particularly, the present invention relates to a process for production of in-vivo refolded recombinant humanized biosimilar Ranibizumab antibody fragment in a soluble form in the cytoplasm of a microbial expression system. The present process provides an increased yield of the recombinant Ranibizumab accompanied with a reduction in overall manufacturing time for the production of rHu Ranibizumab in its native form to three days.

11 Claims, 13 Drawing Sheets
Specification includes a Sequence Listing.

CLONING AND EXPRESSION OF IN VIVO REFOLDED ANTIBODY FRAGMENT

CROSS-REFERENCE TO RELATED APPLICATIONS

This application is a national phase application under 35 U.S.C. § 371 of International Application No. PCT/IN2020/050312 filed 1 Apr. 2020, which claims priority to Indian Patent Application number 201911013248 filed 2 Apr. 2019. The entire contents of each of the above-referenced disclosures is specifically incorporated herein by reference without disclaimer.

INCORPORATION BY REFERENCE OF SEQUENCE LISTING

The instant application contains a Sequence Listing which has been submitted electronically in ASCII format and is hereby incorporated by reference in its entirety. Said ASCII copy, created on Oct. 1, 2021, is named "RCYPP0059US_SeqListing.txt" and is 6,596 bytes in size.

FIELD OF THE INVENTION

The present invention relates to a process for production of in-vivo refolded antibody fragments in a soluble form in the cytoplasm of a microbial expression system. More particularly, the present invention relates to a process for production of in-vivo refolded recombinant humanized biosimilar Ranibizumab antibody fragment in a soluble form in the cytoplasm of the microbial expression system.

BACKGROUND AND PRIOR ART OF THE INVENTION

Time and cost-effective manufacturing of target therapeutic proteins is a vital aspect in the success of the biosimilar industry. A recent trend in biopharmaceutical research and development is more focused on development of antibody fragments. Antibody fragments offer certain advantages over full-size monoclonal antibody therapeutics such as improved and deep tumour penetration, and binding to specific epitopes which are not accessible to full-size mAb's.

Antibody fragments are small and un-glycosylated proteins, thus, their production in microbial expression systems is simpler and is comparatively more economically viable than conventional mammalian cell culture systems used to produce full-size monoclonal antibodies and other biologics. The cytoplasm of wild-type E. coli strains has reducing properties and thus sulphur groups present on cysteine amino acids are in a reduced form i.e. —SH form. Under such reducing conditions prevalent in the cytoplasm, disulfide bonds do not normally form and as a result, most antibodies expressed therein accumulate in a misfolded and inactive state.

Expressing recombinant proteins like antibody fragments in the form of inclusion bodies imposes a great obstacle in production and purification using microbial hosts. Inclusion bodies need extensive processing involving cell isolation, solubilization, refolding and purification to produce bioactive proteins. In spite of new developments in understanding structural details of proteins in inclusion bodies, solubilization and refolding are still carried out in empirical ways leading to poor recovery of the functional protein.

Indian Patent Application number 201711017654 discloses an upstream process for producing in-vitro refolded recombinant humanized Ranibizumab and also discloses a duet vector for expression of rHu Ranibizumab (i.e. bicistronic expression). However, the entire process requires 9 days for upstream and refolding of the protein and the process yield is 30.00±5.00%.

Indian Patent Application number 201711010410 reports a downstream purification technique covering sequential multimodal chromatography purification steps to eliminate product related impurities, host cell proteins and host cell nucleic acids followed by diafiltration and ultrafiltration to obtain purified rHu Ranibizumab.

The overexpression of heterologous proteins in a reducing environment of the cytoplasm of E. coli leads to formation of inactive and insoluble protein aggregates called inclusion bodies. These inclusion bodies need to be subjected to solubilization and refolding to obtain an active protein forms. Existing manufacturing protocol for rHu Ranibizumab requires an in-vitro refolding step or clone engineering for the secretion of the active protein form across one or more biological membranes. The in-vitro refolding step contributes to a major portion of overall manufacturing cost and is a time-consuming process which requires about ~120 hours, i.e. about 5 days. The transport of an expressed protein to the oxidative periplasm for disulfide bond formation has three key limitations:

periplasm accounts for only about $\frac{1}{5}^{th}$ of the total cell volume,
capacity of secretion of a target protein from cytoplasm to the periplasm can be easily overloaded, and
multi-disulfide containing proteins are subjected to incorrect folding which leads to aggregation and formation of inclusion bodies.

Literature shows the possibility of expressing refolded and biologically active form of a recombinant protein in the cytoplasm of E. coli, using genetically engineered strains of E. coli. Origami™ (DE3), Rosetta-gami™ (DE3), SHuffle® T7 (DE3) and SHuffle® T7 Express (DE3) are examples of such redox mutant strains which are capable of cytoplasmic expression of an active form of a protein. These strains differ in the type of mutations responsible for expressing the active form of a protein. In wild-type E. coli, the reducing nature of cytoplasm is due to action of two key enzymes namely, thioredoxin reductase (trxB) and glutaredoxin reductase (gor). E. coli Origami™ (DE3) strain is a trxB, gor, and AhpC (peroxidase) mutant strain, lacking expression of disulfide bond isomerase whereas the E. coli SHuffle strains are trxB, gor, AhpC mutant strain, which constitutively overexpress the cytoplasmic disulfide bond isomerase (DsbC).

FA113 strain (Origami™ (DE3)) has been used for higher level cytoplasmic expression of mouse antibody fragments 2C5 and 5H4 to produce significantly higher expression levels of an active protein. Anna Gaciarz et al (*Microbial cell factories*. 15 (22), 2016) employed an alternative approach to produce a soluble bioactive antibody fragment (42 mg/L) in the cytoplasm using a CyDisCo system. This system involves co-expression of catalysts for disulfide bond formation usually sulfhydryl oxidase, Erv1p and disulfide bond isomerization namely DsbC or PDI without altering the reductive pathways in the cytoplasm. Bo Kong and Grace L. G. (Soluble Expression of Disulfide Bond Containing Proteins FGF15 and FGF19 in the Cytoplasm of *Escherichia coli*. PLOS ONE. 9 (1), e85890, 2014) used redox mutant Rosetta-gami™ 2 (DE3) and SHuffle® T7 Express (DE3) strains for cytoplasmic expression of soluble fibroblast growth factors FGF19 and FGF15, both containing two disulfide bonds. They used TRX fusion tags to enhance the amount of soluble protein, however, they were unsuccessful in expressing FGF15 in a refolded and bioactive form even though it shares about 50% sequence homology with FGF19. The aforesaid studies are indicative that conditions employed for synthesis of a soluble bioactive form of a recombinant protein are not suitable for synthesis of other recombinant proteins.

Mehrnoosh F. et al (*Avicenna Journal of Medical Biotechnology.* 8 (1), 16-22, 2016) attempted the production of Reteplase in a soluble form in Rosetta-gami™ B (DE3) and SHuffle® T7 (DE3) however; the target protein was expressed as inclusion bodies and was not obtained in a soluble form.

Although there are several existing reports on using various *E. coli* expression systems for cytoplasmic expression of active proteins, the selection of an expression system and production of a multi-domain recombinant protein like an antibody fragment is challenging and generally an empirical task with trial and error experimentation.

Therefore, there is a need in the art to provide a process which circumvents the in-vitro refolding step by employing redox mutant microbial host cell which allow the in-vivo formation of a refolded rHu Ranibizumab molecule in an oxidative cytoplasm and a process for the efficient recovery of Ranibizumab from such a microbial host cell.

OBJECT OF THE INVENTION

An objective of the present invention is to provide a process that circumvents the in-vitro refolding step in synthesis of antibody fragments and employs a microbial host cell for expression of said antibody fragments in the cytoplasm in a soluble form.

Another objective of the present invention is to provide a process for synthesis of antibody fragments employing atleast a microbial host cell which allows the in-vivo formation of refolded antibody fragments such as biosimilar rHu Ranibizumab in an oxidative cytoplasm.

Still another objective of the present invention is to provide a process for the in-vivo expression of antibody fragments in high yield.

SUMMARY OF THE INVENTION

With a view to reduce the cost incurred and excessive time consumed in the synthesis of recombinant humanized Ranibizumab on account of in-vitro refolding step employed, the present invention provides a process for production of in-vivo refolded antibody fragment in a soluble form in the cytoplasm of a microbial expression system.

In an aspect, the present invention provides a process for expression and recovery of an in-vivo refolded recombinant antibody fragment comprising;
  a. providing a microbial host cell overexpressing disulfide isomerase with non-expression of enzymes for reducing ability of cytoplasm, said cell comprising a DNA construct encoding light and heavy chain of a recombinant antibody fragment;
  b. culturing said microbial host cell of step (a) in a complex nutrient medium comprising glycerol at 30° C., pH 7 up to an optical density in the range of 20.0 to 25.0 to obtain a culture;
  c. reducing temperature of the culture to a range of 15° C. to 24° C. and adding IPTG to said culture to induce expression to obtain a culture broth comprising in-vivo refolded recombinant antibody fragment;
  d. centrifuging the culture broth of step (c) to obtain a cell mass;
  e. disrupting the cell mass of step (d) to obtain a cell lysate;
  f. centrifuging the cell lysate of step (e) to obtain a first supernatant;
  g. precipitating the first supernatant obtained in step (f) at pH 4.0 followed by centrifugation to obtain a second supernatant;
  h. subjecting the second supernatant of step (g) to ultrafiltration to obtain the in-vivo refolded recombinant antibody fragment in a retentate fraction;
  i. subjecting said retentate fraction of step (h) to a multimodal chromatography and an affinity chromatography to obtain the purified in-vivo refolded recombinant antibody fragment.

Accordingly, the present invention provides a process for production of a recombinant antibody fragment in a soluble form in the cytoplasm of a microbial expression system, comprising;
  (i) constructing a duet vector encoding light chain and heavy chain of a recombinant antibody fragment;
  (ii) transforming the duet vector of step (i) into a host cell selected from the group consisting of *E. coli* SHuffle® T7 (DE3) and SHuffle T7 Express (DE3);
  (iii) culturing the host cell in a shake flask under process parameters at a shake flask level;
  (iv) performing high cell density fermentation of the host cell at a fermenter scale for expression of in-vivo refolded soluble recombinant antibody fragment in cytoplasm of the host cell.

More particularly, the present invention provides a process for production of biosimilar recombinant humanized Ranibizumab antibody fragment in a soluble form in the cytoplasm of a microbial expression system. The present invention provides light and heavy chains of rHu Ranibizumab getting associated with each other in-vivo i.e. intra-chain disulfide bonds within light and heavy chains and inter-chain disulfide bonds between the two chains are formed inside the host cell cytoplasm.

In another aspect, the present invention provides a microbial expression system possessing an oxidative cytoplasm as genes trxB and gor expressing enzymes responsible for cytoplasm's reducing ability namely, thioredoxin reductase and glutaredoxin reductase respectively, have been mutated. Further, the present invention provides overexpression of disulfide isomerase (DsbC) in the cytoplasm of these microbial expression system. DsbC breaks non-native disulfide bonds that are formed and acts as a chaperone for formation of native disulfide bonds.

Advantageously, the present process provides an increased yield of rHu Ranibizumab accompanied with a reduction in overall manufacturing time for production of rHu Ranibizumab in its native form to three days.

BRIEF DESCRIPTION OF THE DRAWINGS

FIG. 5 depicts SDS-PAGE analysis of the precipitate obtained post isoelectric point based precipitation.

FIG. 6 depicts Western blotting analysis of partially purified supernatant obtained from shake flask culture system.

BRIEF DESCRIPTION OF THE SEQUENCE LISTING

Figure 1:
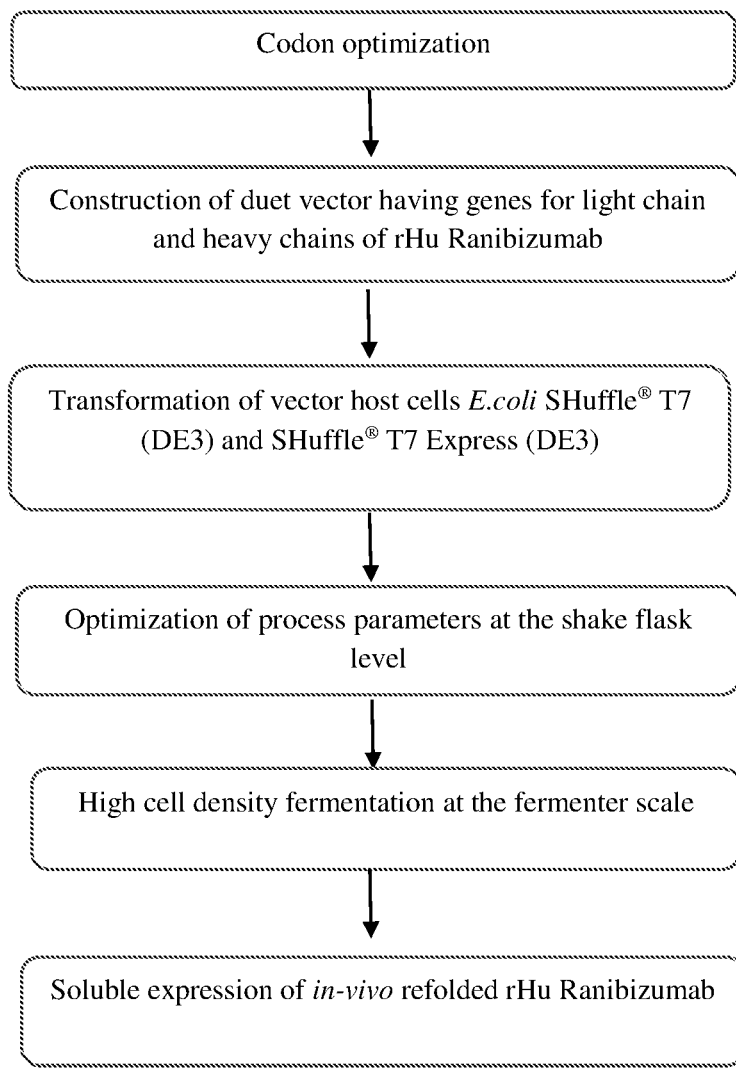
FIG. 1 depicts a novel cloning, expression and in-vivo refolding platform for biosimilar rHu Ranibizumab

The invention can be understood in depth from the detailed description provided below along with the list of sequences which forms a part of the present application.

The sequence descriptions and sequence listing attached hereto obey with the rules governing nucleotide and/or amino acid sequence disclosures in patent applications.

SEQ ID NO.1: Nucleotide sequence encoding heavy chain of Ranibizumab (721 bp)
SEQ ID NO.2: Amino acid sequence of heavy chain of Ranibizumab (231 aa)
SEQ ID NO.3: Nucleotide sequence encoding light chain of Ranibizumab (669 bp)
SEQ ID NO.4: Amino acid sequence of light chain of Ranibizumab (214 aa)

DETAILED DESCRIPTION OF THE INVENTION

The invention will now be described in detail in connection with certain preferred and optional embodiments, so that various aspects thereof may be more fully understood and appreciated.

Source of biological material: *E. coli* SHuffle® T7 (DE3) and *E. coli* SHuffle® T7 Express (DE3) expression systems were procured from New England Biolabs Inc., USA (Cat. No. C3026J and C3029J respectively).

The amino acid sequence of light chain and heavy chain of rHu Ranibizumab was retrieved from drug bank and codon optimization was performed (Accession No.: DB01270). The amino acid sequence of heavy chain of Ranibizumab is as set forth in SEQ ID NO: 2. The amino acid sequence of light chain of Ranibizumab is as set forth in SEQ ID NO: 4.

Accordingly, the present invention relates to a process for expression and recovery of an in-vivo refolded recombinant antibody fragments, wherein the resultant recombinant antibody fragments are obtained in high yield.

The present invention provides a process for expression and recovery of an in-vivo refolded recombinant antibody fragment comprising:
  a. providing a microbial host cell overexpressing disulfide isomerase with non-expression of enzymes for reducing ability of cytoplasm, said cell comprising a DNA construct encoding light and heavy chain of a recombinant antibody fragment;
  b. culturing said microbial host cell of step (a) in a complex nutrient medium comprising glycerol at 30° C., pH 7 to obtain a culture;
  c. reducing temperature of the culture and adding IPTG to said culture to induce expression to obtain a culture broth comprising in-vivo refolded recombinant antibody fragment;
  d. centrifuging the culture broth of step (c) to obtain a cell mass;

e. disrupting the cell mass of step (d) to obtain a cell lysate;
f. centrifuging the cell lysate of step (e) to obtain a first supernatant;
g. precipitating the first supernatant of step (f) at pH 4.0 followed by centrifugation to obtain a second supernatant;
h. subjecting the second supernatant of step (g) to ultrafiltration to obtain the in-vivo refolded recombinant antibody fragment in a retentate fraction;
i. subjecting said retentate fraction of step (h) to a multimodal chromatography and an affinity chromatography to obtain the purified in-vivo refolded recombinant antibody fragment.

In an embodiment of the present invention, there is provided a process for expression and recovery of an in-vivo refolded recombinant antibody fragment, wherein the recombinant antibody fragment is a fragment of recombinant Human Ranibizumab.

In another embodiment of the present invention, there is provided a process for expression and recovery of an in-vivo refolded recombinant antibody fragment, wherein the microbial host cell is an *E. coli* host cell.

In still another embodiment of the present invention, there is provided a process for expression and recovery of an in-vivo refolded recombinant antibody fragment, wherein the *E. coli* host cell is selected from the group consisting of SHuffle T7 (DE3) and SHuffle T7 Express (DE3) cells.

In an embodiment of the present invention, there is provided a process for expression and recovery of an in-vivo refolded recombinant antibody fragment, wherein in step (c), the temperature of the culture is reduced from 30° C. to a temperature in the range of 15° C. to 24° C. during induction.

In another embodiment of the present invention, there is provided a process for expression and recovery of an in-vivo refolded recombinant antibody fragment, wherein IPTG is added at a concentration in the range of 0.55 mM to 1 mM.

In still another embodiment of the present invention, there is provided a process for expression and recovery of an in-vivo refolded recombinant antibody fragment, wherein the process is performed with dissolved oxygen (DO) at a concentration of 30% of air saturation with agitation in the range of 300 to 1000 rpm and $O_2$ enrichment from 0 to 90%.

In yet another embodiment of the present invention, there is provided a process for expression and recovery of an in-vivo refolded recombinant antibody fragment, wherein the host cell is induced at an optical density in the range of ~20.0 to 25.0 in mid-log phase growth phase.

In still another embodiment of the present invention, there is provided a process for expression and recovery of an in-vivo refolded recombinant antibody fragment, wherein the glycerol concentration in the complex nutrient medium is in the range of 30 g/L to 35 g/L.

In an embodiment of the present invention, there is provided a process for expression and recovery of an in-vivo refolded recombinant antibody fragment, wherein the affinity chromatography is performed in a bind and elute mode with binding at a higher pH and elution at a lower pH.

In another embodiment of the present invention, there is provided a process for expression and recovery of an in-vivo refolded recombinant antibody fragment, wherein the higher pH for binding is at 8.5 to 10.5 and the lower pH for elution is at 2.5 to 4.5. The present invention provides a process for expression and recovery of an in-vivo refolded recombinant antibody fragments comprising;

a) providing a microbial host cell overexpressing disulfide isomerase with non-expression of enzymes for reducing ability of cytoplasm, said cell comprising a DNA construct encoding light and heavy chain of a recombinant antibody fragment;
b) culturing said microbial host cell of step (a) in a complex nutrient medium comprising glycerol at 30° C., pH 7 up to an optical density in the range of 20.0 to 25.0 to obtain a culture;
c) reducing temperature of the culture to a range of 15° C. to 24° C. and adding IPTG to said culture to induce expression to obtain a culture broth comprising in-vivo refolded recombinant antibody fragment;
d) centrifuging the culture broth of step (c) to obtain a cell mass;
e) disrupting the cell mass of step (d) to obtain a cell lysate;
f) centrifuging the cell lysate of step (e) to obtain a first supernatant;
g) precipitating the first supernatant of step (f) at pH 4.0 followed by centrifugation to obtain a second supernatant;
h) subjecting the second supernatant of step (g) to ultrafiltration to obtain the in-vivo refolded recombinant antibody fragment in a retentate fraction;
i) subjecting said retentate fraction of step (h) to a multimodal chromatography and an affinity chromatography to obtain the purified in-vivo refolded recombinant antibody fragment.

The present process for synthesis and recovery of in-vivo refolded recombinant antibody fragment is extended to the synthesis of antibodies, recombinant antibodies with multiple domains and recombinant proteins having therapeutic applications.

In an embodiment, the present process for synthesis and recovery of in-vivo refolded recombinant antibody fragment is employed for the synthesis of recombinant antibody fragment of recombinant humanized antibody fragment of Ranibizumab, Abciximab and Certolizumab.

In a preferred embodiment, the present invention provides a process for expression and recovery of in-vivo refolded recombinant Ranibizumab comprising;

a) providing a microbial host cell overexpressing disulfide isomerase with non-expression of enzymes for reducing ability of cytoplasm, said cell comprising a DNA construct encoding light and heavy chain of Ranibizumab;
b) culturing said microbial host cell of step (a) in a complex nutrient medium comprising glycerol at 30° C. with pH 7 up to an optical density in the range of 20.0 to 25.0 to obtain a culture;
c) reducing temperature of the culture to a range of 15° C. to 24° C. and adding IPTG to said culture to induce expression to obtain a culture broth comprising in-vivo refolded rHuRanibizumab;
d) centrifuging the culture broth of step (c) to obtain a cell mass;
e) disrupting the cell mass of step (d) to obtain a cell lysate;
f) centrifuging the cell lysate of step (e) to obtain a first supernant;
g) precipitating the first supernatant of step (f) at pH 4.0 followed by centrifugation to obtain a second supernatant;
h) subjecting the second supernatant of step (g) to ultrafiltration to obtain the in-vivo refolded rHu Ranibizumab in a retentate fraction;

i) subjecting said retentate fraction of step (h) to a multimodal chromatography and an affinity chromatography to obtain the purified in-vivo refolded rHu Ranibizumab.

In keeping with step (a) of the present process, the present invention provides a bacterial expression vector which is constructed by cloning the nucleotide sequence encoding light chain of Ranibizumab having the polynucleotide sequence as set forth in SEQ ID NO: 3 and nucleotide sequence encoding heavy chain having the polynucleotide sequence as set forth in SEQ ID NO: 1. This bicistronic vector carrying the genes encoding light chain and heavy chain is then transformed in a bacterial host cell overexpressing disulfide isomerase with non-expression of enzymes involved in the reducing ability of the cytoplasm. The host cell is selected from a bacterial or a yeast host cell. The present invention provides use of competent host cells of *E. coli* selected from the group consisting of SHuffle® T7 (DE3) and SHuffle® T7 Express (DE3) expression systems.

Based on the antibiotic selection marker, positively transformed cells are isolated from the plates and are used for checking the expression of the protein of interest, i.e. the antibody fragments of recombinant Ranibizumab.

In another preferred embodiment, the present invention provides a process for the production of antibody fragments in a soluble form in the cytoplasm of a microbial expression system comprising the steps;
 (i) constructing a duet vector comprising the genes encoding light chain and heavy chain of a recombinant antibody fragment;
 (ii) transforming the duet vector of step (i) into a host cell selected from the group consisting of *E. coli* SHuffle® T7 (DE3) and SHuffle® T7 Express (DE3);
 (iii) culturing the host cell in a shake flask under process parameters at a shake flask level; and
 (iv) performing high cell density fermentation of the host cell at a fermenter scale for expression of in-vivo refolded soluble recombinant antibody fragment in cytoplasm of the host cell.

Figure 2:
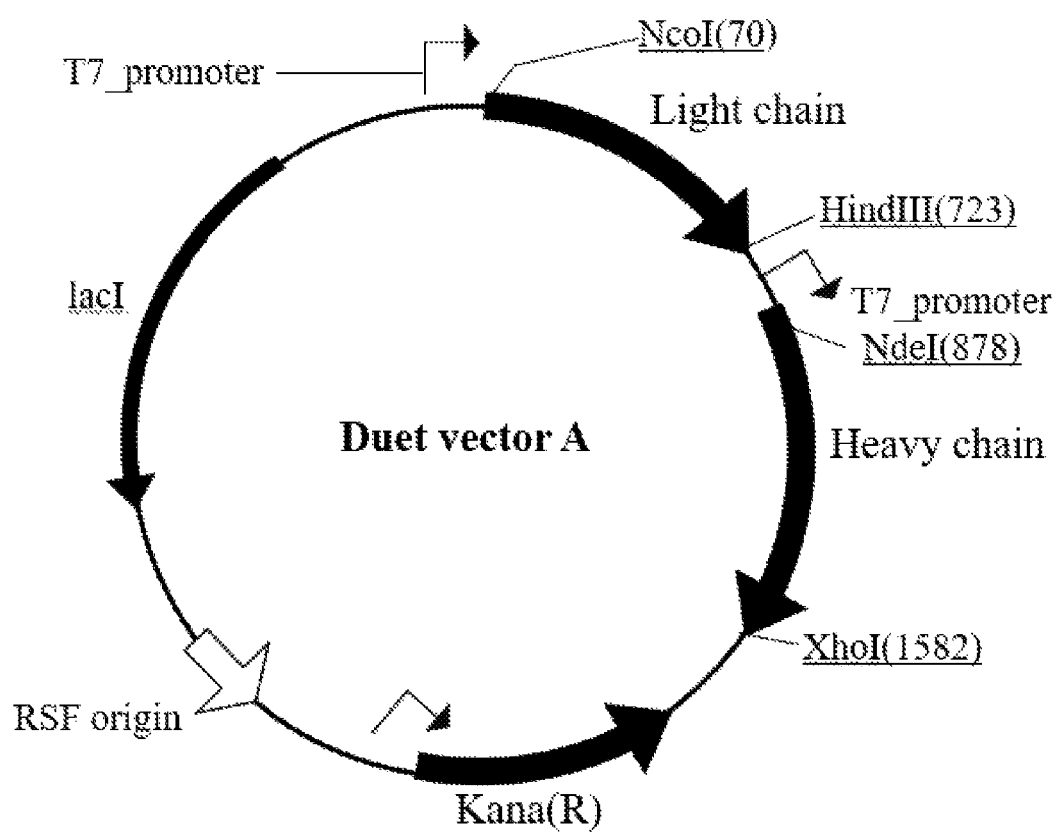
FIG. 2 depicts duet vector A comprising the gene encoding the light and heavy chain of biosimilar rHu Ranibizumab
Figure 9:
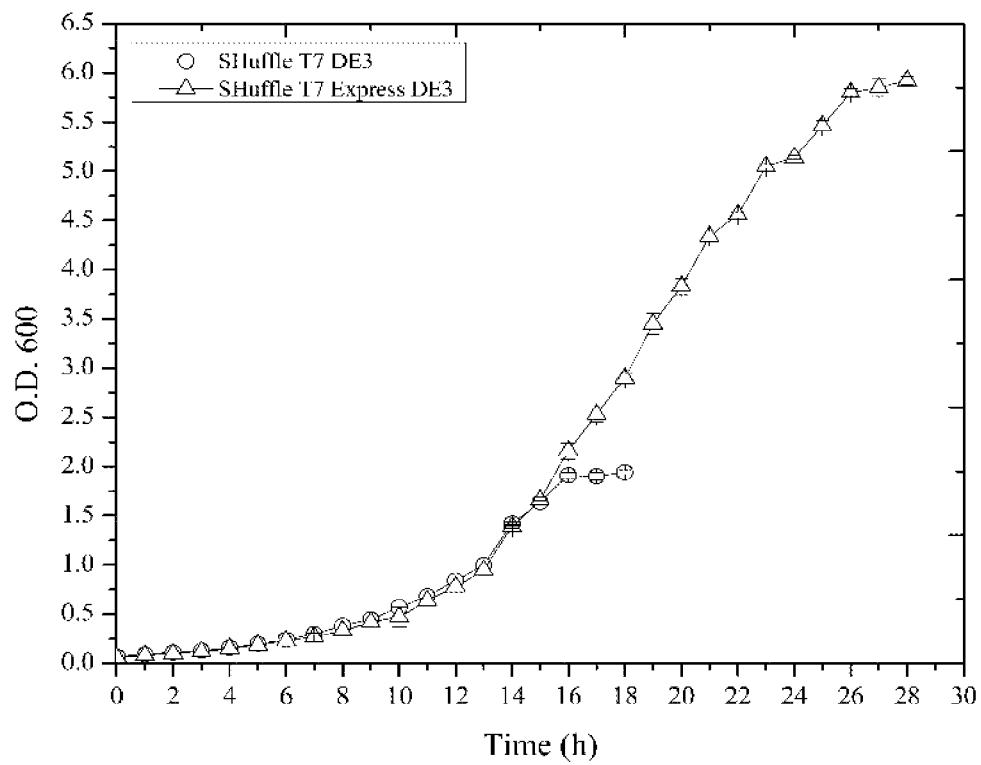
FIG. 9 depicts growth characteristics of *E. coli* SHuffle® T7 (DE3) and SHuffle® T7 Express (DE3) in a chemically defined minimal media.
Figure 10:
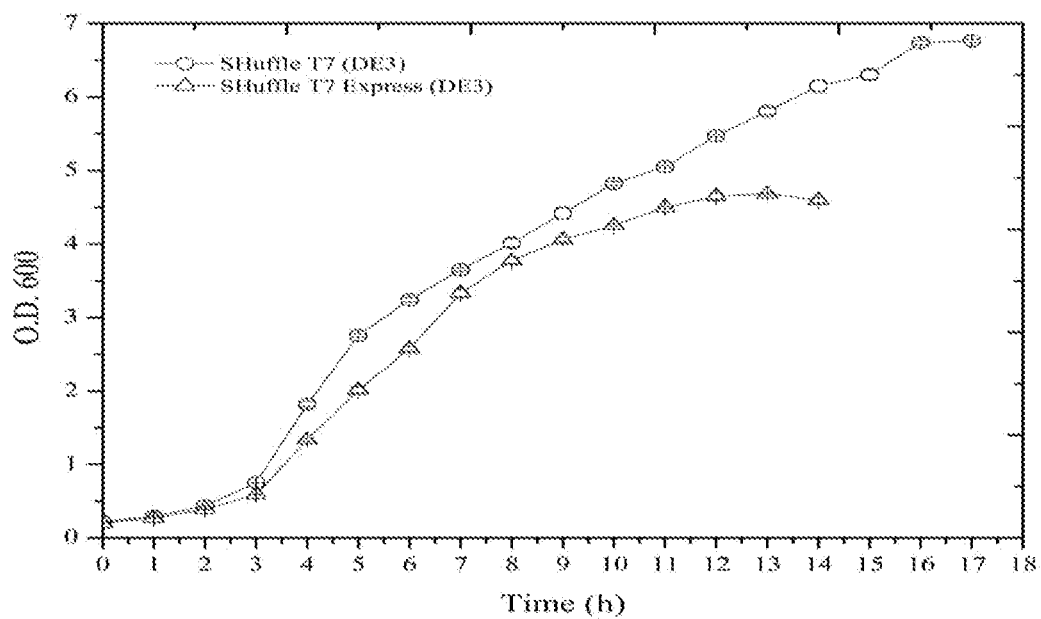
FIG. 10 depicts growth characteristics of *E. coli* SHuffle® T7 (DE3) and SHuffle® T7 Express (DE3) in a modified complex media.
Figure 11:
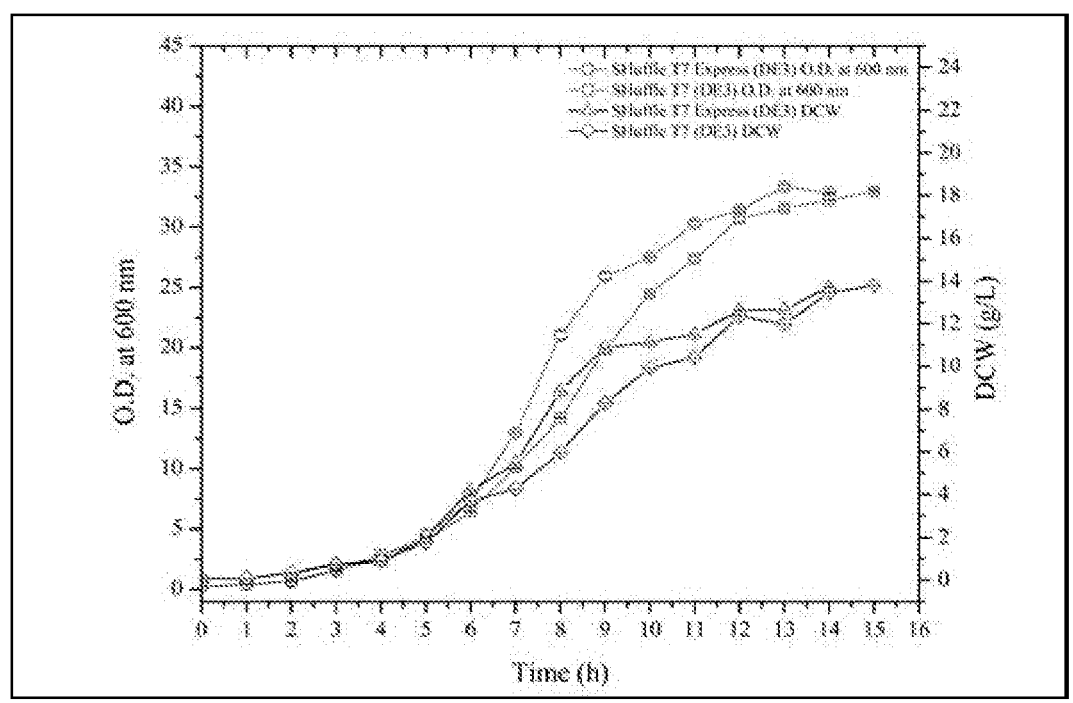
FIG. 11 depicts the time-course of optical density at 600 nm and DCW (g $L^{-1}$) for batch mode fermentation of recombinant *E. coli* SHuffle T7 (DE3) and SHuffle T7 Express (DE3) in a modified complex media.
Figure 12:
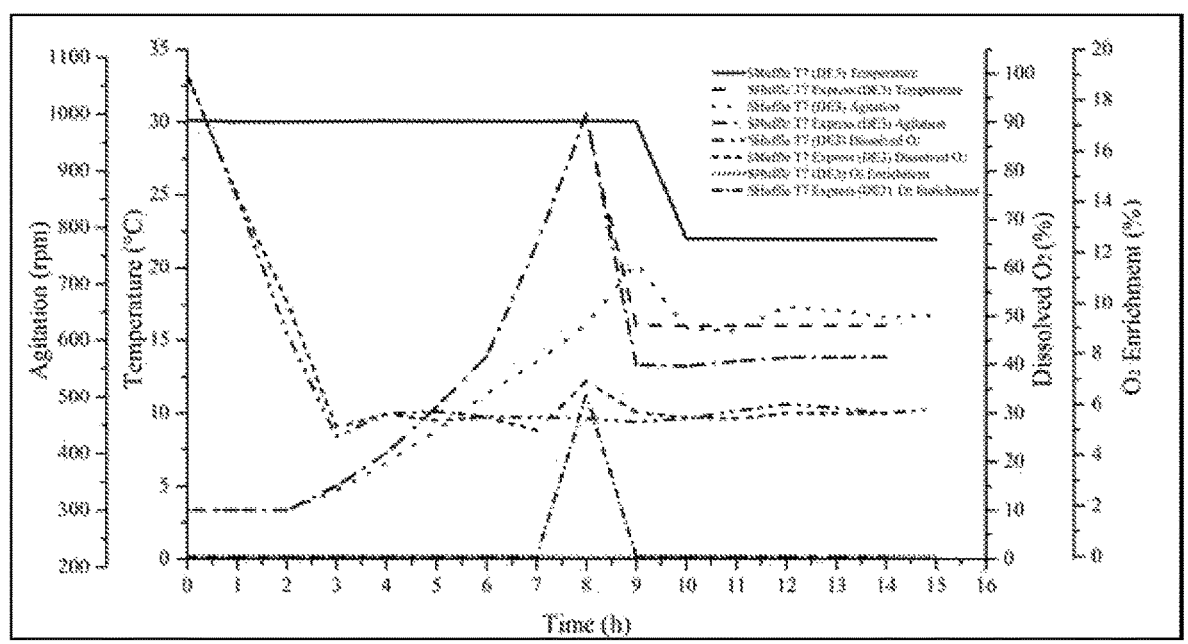
FIG. 12 depicts the time-course of stirrer speed (rpm), oxygen flow rates (%) and dissolved $O_2$ concentration (%) for batch mode fermentation of recombinant *E. coli* SHuffle T7 (DE3) and SHuffle T7 Express (DE3) in a modified complex media.

Accordingly, a pRSF duet vector construct comprising the gene encoding light chain and heavy chain was used to transform competent SHuffle® T7 (DE3) and SHuffle® T7 Express (DE3) expression systems. FIG. 2 illustrates the design of the duet vector A for the expression of light and heavy chain genes of rHu Ranibizumab. The present invention circumvents the in-vitro refolding step by employing the two aforesaid microbial expression system namely, *E. coli* SHuffle® T7 (DE3) and SHuffle® T7 Express (DE3). Said microbial expression system comprises an oxidative cytoplasm as the genes trxB and gor expressing two enzymes responsible for reducing ability of the cytoplasm namely, thioredoxin reductase and glutaredoxin reductase respectively, have been mutated. FIGS. 9 and 10 shows growth characteristics of the two redox mutant microbial expression system in chemically defined minimal media and modified complex media respectively. It is evident from a comparison of FIGS. 9 and 10, respectively, that the modified complex media consisting of a nutritionally rich Tartoff Hobbs HiVeg Terrific broth and glycerol is the much preferred medium for efficient growth of the redox mutant *E. coli* microbial expression system as indicated in the extended log phase of the cell culture. This efficient growth phase using the modified complex medium is reflected in the 1.5 to 2 folds increase in the in-vivo refolded rHu Ranibizumab expression levels which is observed in the modified complex media as compared to chemically defined minimal media.

In an embodiment, the present invention provides an overexpression of protein disulfide isomerase known as DsbC in the cytoplasm of these microbial expression system. The DsbC breaks non-native disulfide bonds that are formed and acts as a chaperone for the formation of native disulfide bonds. The light and heavy chains of rHu Ranibizumab get associated with each other in-vivo i.e. the intrachain disulfide bonds within the light and heavy chains and inter-chain disulfide bonds between the two chains are formed inside the host cell cytoplasm. Cytoplasmic expression of the refolded rHu Ranibizumab offers an attractive high-throughput alternative for Ranibizumab manufacturing since it can easily replace the rate-limiting in-vitro refolding step currently required to obtain the biologically active form of rHu Ranibizumab.

In yet another embodiment, the present invention provides a bioreactor scale process for dissolved oxygen (DO) which was maintained at 30% of air saturation using an agitation cascade from 300 to 1000 rpm and 02 enrichment from 0 to 90%. The pH was controlled at ~7.0 by addition of 15% v/v aqueous ammonia and 30% v/v orthophosphoric acid. Foaming in the bioreactor was controlled by addition of 20% v/v antifoam reagent. When the bacterial culture reached an optical density of about ~20.0 to 25.0 i.e. mid-log phase, the temperature was reduced to 22° C. for SHuffle T7 (DE3) and 16° C. for SHuffle T7 Express (DE3) and the culture was induced using 0.55 mM IPTG.

The process parameters of steps (b) and step (c) of the present process disclosed in the preferred embodiment for the synthesis and recovery of in-vivo refolded recombinant antibody fragments are arrived at by the present inventors with respect to the microbial expression system and the recombinant antibody to be expressed. The process parameters have a significant influence on the expression of the recombinant antibody in a soluble form. Experimentation was undertaken to study the impact of various process parameters on the soluble expression and to determine the optimal conditions for enhanced yields of in-vivo refolded rHu Ranibizumab.

At the shake flask scale, *E. coli* host cells carrying the nucleotide construct expressing the light chain and heavy chain of biosimilar rHu Ranibizumab were cultivated and transferred into LB broth and incubated at 30° C. and 225 rpm. After achieving an optical density of 0.5-0.6 at 600 nm, the *E. coli* culture was induced with 1 mM IPTG. Cells were harvested after an eight hours induction period and the culture broth was subjected to centrifugation at 6000 rpm at 10° C. for 30 minutes. The cell biomass thus obtained was re-suspended in a lysis buffer comprising 100 mM Tris, 50 mM NaCl, 5 mM EDTA and the cell suspension was subjected to sonication in a 3-minute cycle. Post cell lysis, samples were subjected to centrifugation at 9000 rpm, 6° C. for 15 minutes. The supernatant fraction was subjected to subsequent partial purification for confirming soluble protein expression. Shake flask level Shuffle® T7 (DE3) and Shuffle® T7 Express (DE3) *E. coli* fermentation lead to an optical density of 3.96±0.05 and 3.46=0.07 at 600 nm with 4.9±0.25 g/l and 4.7±0.70 g/l biomass, respectively.

In another preferred embodiment, the present invention provides a process for the purification and recovery of the recombinant Ranibizumab comprising;
 a) centrifuging a culture broth recovered after culturing host cells expressing in-vivo refolded recombinant Ranibizumab to obtain a cell mass;
 b) disrupting the cell mass of step (a) to obtain a cell lysate;

c) centrifuging the cell lysate of step (b) to obtain a first supernatant;
d) precipitating the first supernatant obtained in step (c) at pH 4.0 followed by centrifugation to obtain a second supernatant;
e) subjecting the second supernatant of step (d) to ultrafiltration to obtain the in-vivo refolded recombinant Ranibizumab in a retentate fraction;
f) subjecting said retentate fraction of step (e) to a multimodal chromatography and an affinity chromatography to obtain the purified in-vivo refolded recombinant Ranibizumab.

Figure 3:
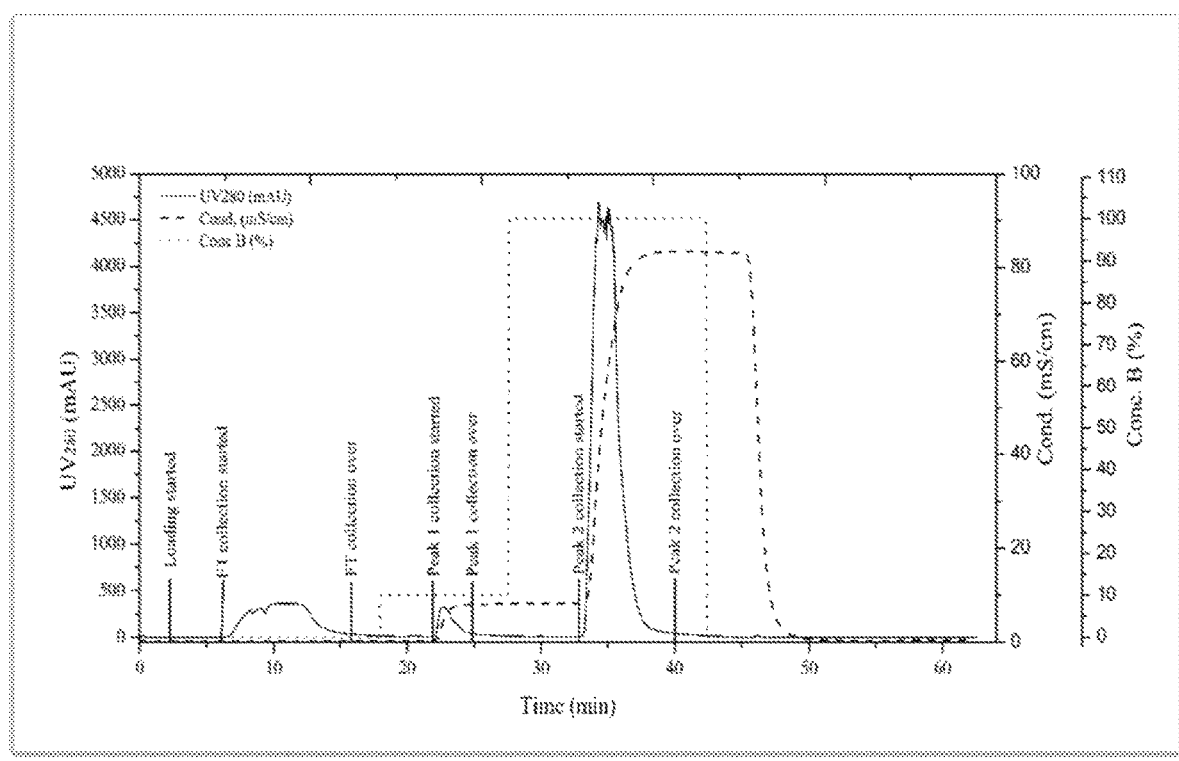
FIG. 3 depicts multimodal chromatography based partial purification of in-vivo refolded biosimilar rHu Ranibizumab FIG. 4(*a*) depicts SDS-PAGE analysis of partially purified supernatant containing rHu Ranibizumab in a shake flask culture system; wherein Lane 1: Innovator Ranibizumab molecule, Lane 2: *E. coli* SHuffle® T7 (DE3) supernatant, Lane 3: *E. coli* SHuffle® T7 Express (DE3) supernatant.

According to the aforementioned process steps, the cell biomass is obtained by centrifuging the culture broth at 6000 rpm, 10° C. for 30 minutes. For purification, lab scale experiments were performed using an ÄKTA Purifier chromatography system. Chromatography column (6.6×450 mm) was used to pack 15.0±0.2 cm BAKERBOND™ XWP 500 Poly PEI-35 multimodal resin. The chromatography column was equilibrated using the selected equilibration buffer i.e. 20 mM Tris pH 9.0 (5-10 CV). Cell-free supernatant obtained post cell lysis was buffer exchanged into the aforementioned equilibration buffer and was then injected into the chromatography column using a sample pump. After sample loading, the unbound protein sample was removed using equilibration buffer wash step (5 CV). Elution step consisted of selective salt based elution gradient involving a step gradient of 10% elution buffer followed by a step gradient to 100% of elution buffer. The output from the chromatography column was monitored using pH, conductivity and UV detection at 280, 260 and 215 nm. FIG. 3 shows the chromatogram for the partial purification of the cell-free supernatant. For complete purification, the cell lysate was subjected to isoelectric precipitation, followed by centrifugation and ultrafiltration of the supernatant and purification of the retentate using the BAKERBOND™ XWP 500 Poly PEI-35 multimodal resin using a salt gradient and CH1-XL affinity matrix in a bind and elute mode through binding at a higher pH and elution at a lower pH resulting in a final purity of 99.44%. Accordingly, the higher pH for binding is at 8.5 to 10.5 and the lower pH for elution is at 2.5 to 4.5

In another embodiment, the present invention provides an increase in expression level of the in-vivo refolded rHu Ranibizumab in the modified complex media as compared to chemically defined minimal media (Table 3) in a range from about 1.5 to 2 folds increase at the shake flask scale.

The affinity chromatography step offers two critical advantages; firstly, the host cell proteins are allowed to flow through as the immobilized ligands recognize the CH1 domain of human IgG antibodies independent of the light-chain iso-type and independent of the source material and secondly, it allows the separation of homodimers formed between the light chains and the heterodimers formed between the light and heavy chains as confirmed by MALDI-TOF MS analysis in FIG. 8. Accordingly, MALDI-TOF MS analysis of the refolded and purified antibody fragment under non-reduced conditions confirmed the intact mass of ~48 kDa identical to that of the Innovator Ranibizumab molecule in FIG. 8(*b*). Further, FIG. 4(*b*) shows the SDS-PAGE analysis of the steps involved in the purification of the target protein from the crude cell lysate to the final purified product.

Accordingly, the overall manufacturing time required for the production of rHu Ranibizumab in its native form has been reduced down from nine to three days by employing this newly developed technology. This leads to a probable productivity enhancement of at least four-fold as compared to the existing in-vitro refolding process.

In yet another preferred embodiment, the present invention provides a process for the expression and recovery of in-vivo refolded rHu Ranibizumab such that the yield of the recombinant Ranibizumab is in the range of 50 mg/L to 90 mg/L at the shake flask scale.

The present process also provides for biosimilarity studies which indicated that the antibody fragments, viz, light and heavy chain of Ranibizumab fragments yielded by the present process are similar to innovator Ranibizumab molecule. This is well reflected in FIG. 7 which depicts RP-HPLC analysis overlay of in-vivo refolded biosimilar rHu Ranibizumab and the innovator Ranibizumab molecule. Therefore, the recombinant Ranibizumab obtained by the present process is safe and efficacious with respect to the Innovator Ranibizumab Molecule.

Advantages of the Present Invention

The present invention provides two microbial expression systems for expression of biosimilar rHu Ranibizumab in a soluble form.

Cytoplasmic expression of the refolded rHu Ranibizumab offers an attractive high-throughput alternative for Ranibizumab manufacturing since it can easily replace the rate-limiting in-vitro refolding step currently required to obtain the biologically active form of Ranibizumab.

The overall manufacturing time required for production of rHu Ranibizumab in its native form has been reduced down from nine to three days by employing the process disclosed by the present invention. This leads to a probable productivity enhancement of at least four-fold to six fold as compared to the existing in-vitro refolding process.

The process yield of the process of the present invention is 45±5.00%.

There is 30.0% cost reduction by using the process of the present invention due to removal of in-vitro refolding.

EXAMPLES

Following examples are given by way of illustration therefore should not be construed to limit the scope of the invention.

Example 1

Cloning of the Nucleotide Sequence Encoding Light Chain and Heavy Chain of rHu Ranibizumab Construction of an expression vector containing genes encoding light chain and heavy chain of rHu Ranibizumab and subsequent transformation of the host cells was done as described below.

(i) Light Chain and Heavy Chain Nucleotide Sequence Construction by Codon Optimization Amino acid sequences of the light chain and heavy chain were taken from drug bank and codon optimization was performed.

(ii) Generation of pRSF Duet Vector for Light Chain and Heavy Chain of rHu Ranibizumab Bacterial expression vector pRSF duet vector was constructed by cloning polynucleotide sequence having sequence as set forth in SEQ ID NO: 3 encoding light chain at 5' end into NcoI/HindIII cloning site preceding by T7 promoter in multiple cloning site I (MCS I) and polynucleotide sequence having sequence as set forth in SEQ ID NO: 1 encoding heavy chain at 5' end into NdeI/XhoI cloning site preceding by T7 promoter in multiple cloning site II (MCS II).

(iii) Transformation of pRSF Duet Vector Comprising the Genes for Light Chain and Heavy Chain in *E. coli* SHuffle T7 (DE3) and SHuffle T7 Express (DE3) Expression Systems (a) Materials: Miller Luria Bertani HiVeg broth (LB broth), SOC growth medium, Luria Bertani HiVeg agar, Tartoff Hobbs HiVeg terrific broth (TB), cobalt chloride, manganese (II) chloride, copper chloride, sodium molybdate dihydrate, zinc acetate dihydrate, ferric citrate monohydrate, thiamine hydrochloride, trizma base and kanamycin solution were purchased from HiMedia Laboratory Private Limited, India. Expression duet vector was purchased from Merck Life Science Private Limited, India. *E. coli* SHuffle® T7 (DE3) and Shuffle® T7 Express (DE3) were purchased from New England Biolabs Inc., USA. Petri dish and 10 µl disposable inoculation loops were purchased from Tarsons Products Private Limited, India. All buffers and growth media were prepared in Milli-Q water. Glacial acetic acid, acetonitrile (HPLC grade), methanol (HPLC grade), sodium acetate (anhydrous), sodium chloride, sodium hydroxide, boric acid, diammonium hydrogen phosphate, citric acid, potassium dihydrogen phosphate, magnesium sulphate, hydrogen peroxide (30%), disodium hydrogen orthophosphate, potassium chloride and nickel ammonium sulphate were purchased from Merck Life Science Private Limited, India. Glycerol was purchased from Promega Corporation, USA. Bromophenol blue, trifluoroacetic acid (TFA), acrylamide, ammonium persulfate, N,N' methylene bisacrylamide, beta-mercaptoethanol, glycine, sodium dodecyl sulfate, sodium salt of ethylenediaminetetraacetic acid (EDTA) and N, N,N', N'-Tetramethylethylenediamine (TEMED were purchased from Sigma Aldrich Co., India. BAKERBOND™ XWP 500 Poly PEI-35 resin was purchased from Avantor Performance Materials Private Limited, India. Goat Anti-Rabbit IgG Secondary antibody (H+L), HRP conjugated was purchased from Thermo Fisher Scientific Private Limited, India. Nitrocellulose membrane, filter papers and fiber pads were purchased from Bio-Rad Laboratories Private Limited, India. The primary antibody used for western blot analysis was raised specifically against rHu Ranibizumab by injecting the innovator Ranibizumab molecule i.e. Lucentis in two female rabbits and the serum was collected post two booster doses of immunization (Intox Private Limited, India). Serum obtained was subjected to Protein A chromatography using MabSelect™ SuRe™ LX from GE Healthcare, USA to purify polyclonal IgG's raised against rHu Ranibizumab.

(b) Equipment: Bacterial culture was incubated using a CIS-24 PLUS shaker from REMI Laboratory Instruments, India. Cells were lysed by using the sonicator Vibracell™ from Sonics and Materials Inc., USA. Bacterial cell separation was achieved using Eppendorf 5804R refrigerated centrifuge, Germany. Measurement of absorbance at 280 nm for protein concentration and at 600 nm for cell density measurement was performed using a Nanodrop™ 2000 from Thermo Scientific, USA and UV-1800 Shimadzu UV Visible spectrophotometer from Shimadzu Analytical Private Limited, Japan respectively. SPD1010 Speedvac™ concentrator was used for concentrating the protein samples for mass analysis. Reversed Phase High-Performance Liquid Chromatography (RP-HPLC) analysis for expressed protein concentration was carried out with a 4.6 mm×250 mm Aeris™ 3.6 µm WIDEPORE XB-C8 column from Phenomenex, USA operated with the Agilent 1200 HPLC system. RP-HPLC data was recorded and analyzed using the Agilent ChemStation software. Mass spectrometry analysis was performed using AB SCIEX TOF/TOF™ 5800 from SCIEX, USA. Data were recorded and analysed using Data Explorer® Software Version 4.11.

(c) Transformation protocol: pRSF duet vector construct comprising genes encoding light chain gene and heavy chain gene was transformed with competent SHuffle® T7 (DE3) and SHuffle® T7 Express (DE3) expression systems. Transformation method comprises: Incubation of 50 µl host cell with 5 µl vector for 30 min on ice, followed by a heat shock at 42° C. for 30 seconds. After the heat shock, cells were again incubated on ice for 5 minutes. 950 µl of SOC medium was then added to a reaction mix followed by an incubation of 60 minutes at 30° C., 300 rpm in a dry bath. 100 µl of the *E. coli* transformants were plated on 30 µg/ml kanamycin containing LB agar plates. Transformed cells containing plates were incubated at 30° C. for 24-48 hours. Based on the antibiotic selection marker, positively transformed cells were isolated from the plates and were used for checking the expression of the protein of interest.

Example 2 rHu Ranibizumab Soluble Expression at Shake Flask Level

Selected transformants of *E. coli* SHuffle® T7 (DE3) and SHuffle® T7 Express (DE3) were tested for refolded rHu Ranibizumab expression. The selected colonies were inoculated into 50 ml LB broth with 30 µg/ml kanamycin. Cells were grown until the optical density at 600 nm reached the value between 1 to 1.2 following which 5 ml of these well-grown colonies were transferred into 100 ml LB broth (secondary culture) and incubated at 30° C. and 225 rpm. After achieving the optical density of 0.5-0.6 at 600 nm, the *E. coli* culture was induced with 1 mM IPTG. Cells were harvested after an eight-hour induction period and the culture broth was subjected to centrifugation at 6000 rpm at 10° C. for 30 minutes. The cell biomass thus obtained was resuspended in lysis buffer (100 mM Tris, 50 mM NaCl, 5 mM EDTA) and the cell suspension was subjected to sonication in a 3-minute cycle (10 seconds pulse on, 20 seconds pulse off). Post cell lysis, samples were subjected to centrifugation at 9000 rpm, 6° C. for 15 minutes. The supernatant fraction was subjected to subsequent partial purification for confirming soluble protein expression. Shake flask level Shuffle® T7 (DE3) and Shuffle® T7 Express (DE3) *E. coli* fermentation lead to an optical density of 3.96±0.05 and 3.46±0.07 at 600 nm with 4.9±0.25 g/l and 4.7±0.70 g/l biomass, respectively.

Example 3

Partial Purification of the In-Vivo Refolded rHu Ranibizumab

Lab scale experiments were performed using an ÄKTA Purifier chromatography system (Amersham Bio-Sciences, Sweden). Omnifit™ (Diba industries, UK) chromatography column (6.6×450 mm) was used to pack 15.0±0.2 cm BAKERBOND™ XWP 500 Poly PEI-35 multimodal resin. The chromatography column was equilibrated using the selected equilibration buffer i.e. 20 mM Tris pH 9.0 (5-10 CV). Cell-free supernatant obtained post cell lysis was buffer exchanged into the aforementioned equilibration buffer and was then injected into the chromatography column using a sample pump. After sample loading, the unbound protein sample was removed using equilibration buffer wash step (5 CV). Elution step consisted of selective salt based elution gradient involving step gradient of 10% elution buffer followed by a step gradient to 100% of elution buffer. The output from the chromatography column was monitored using pH, conductivity and UV detection at 280, 260 and 215 nm. FIG. 3 shows a chromatogram for the purification step for partial purification of the cell-free supernatant.

Example 4

Analytical Assay Development for Characterization of In-Vivo Refolded Biosimilar rHu Ranibizumab Produced at Shake Flask Scale Various orthogonal analytical assays (RP-HPLC, SDS PAGE, Western Blotting and MALDI-TOF-MS) were developed and optimized for characterization of in-vivo refolded rHu Ranibizumab.

(i) Absorbance Measurement for Protein Samples

Total protein post-lysis and chromatography outputs were determined using UV absorbance measurement at 280 nm. All fractions collected were read at 280 nm using Nanodrop™ 2000 and UV-1800 Shimadzu UV Visible spectrophotometer.

(ii) SDS PAGE Analysis of rHu Ranibizumab Samples

Figure 4A:
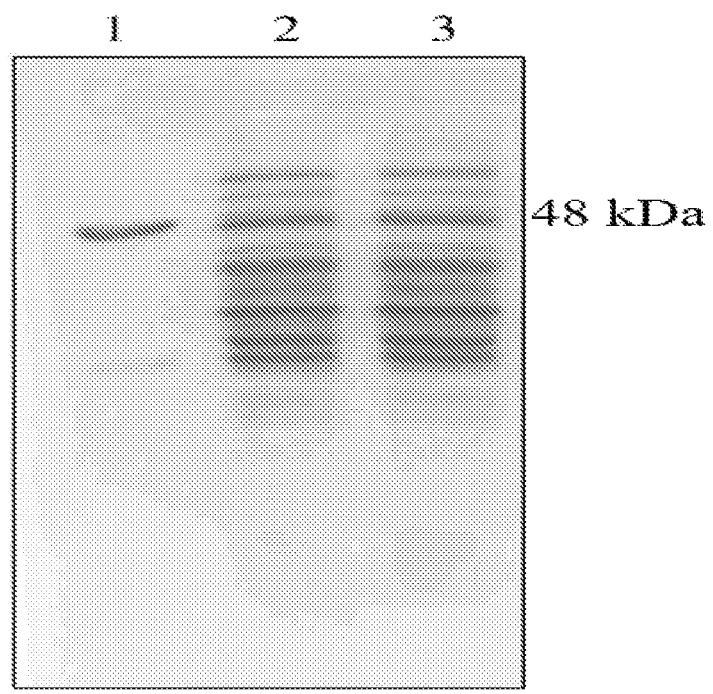
FIG. 4(b) depicts the SDS-PAGE analysis of steps involved in purification of in-vivo refolded rHu Ranibizumab antibody fragment under non-reducing conditions; Lane MW: Standard molecular weight marker, Lane 1: Innovator Ranibizumab molecule, Lane 2: Purified target protein, Lane 3: Multimodal chromatography elute (10% gradient), Lane 4: -, Lane 5: Multimodal chromatography elute (100% gradient), Lane 6: Ultrafiltration retentate post buffer exchange, Lane 7: Affinity chromatography flow-through, Lane 8: Cell lysate.
FIG. 4(c) depicts SDS-PAGE analysis of in-vivo refolded rHu Ranibizumab antibody fragment under non-reducing conditions; Lane MW: Standard molecular weight marker, Lane 1: Innovator Ranibizumab molecule, Lane 2: Purified refolded protein expressed using *E. coli* SHuffle T7 (DE3) host cell, Lane 3: Purified refolded protein expressed using *E. coli* SHuffle T7 Express (DE3) host cell.
Figure 4B:
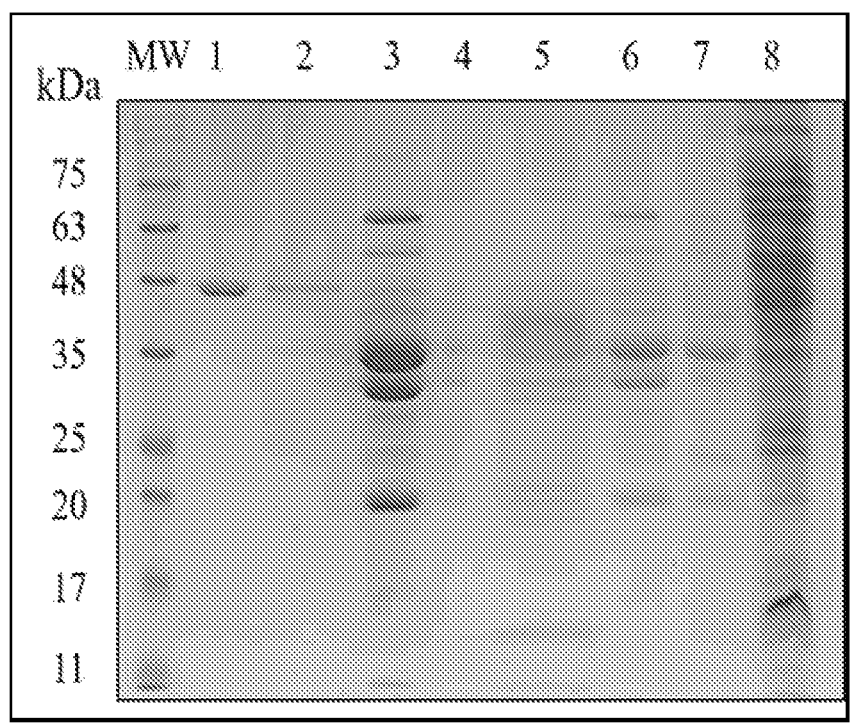
Figure 4C:
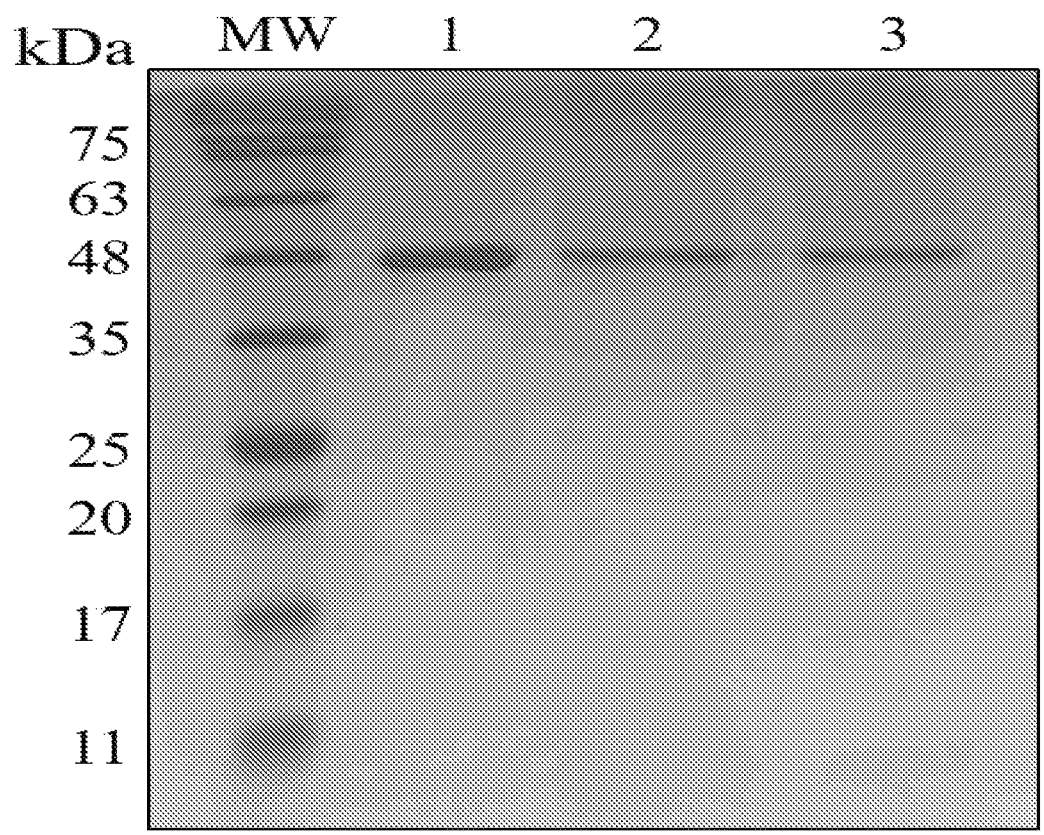

SDS PAGE analysis for identification of expression of in-vivo refolded rHu Ranibizumab in two microbial strains was carried out using 12% (thickness 1 mm) of resolving gel under non-reducing conditions (FIG. 4(a)) at the stacking gel constant voltage 100V and resolving gel constant voltage 80V conditions. Each sample was boiled for 10 min in the starting buffer before being loaded into the gel. 0.05% (w/v) Coomassie brilliant blue G-250 in 4:1:5 (Water:Glacial Acetic acid:Methanol) was used to detect proteins after electrophoretic separation on polyacrylamide gels. The in-vivo refolded rHu Ranibizumab antibody fragment migrated with an expected mobility of ~48 kDa.

(iii) Western Blot Analysis of rHu Ranibizumab

Figure 6A:
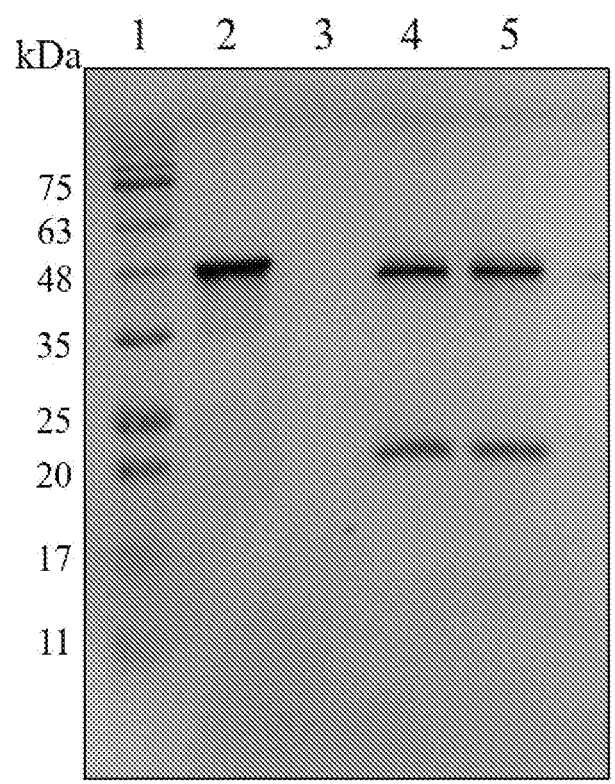
FIG. 6(a); Lane 1: Protein marker, Lane 2: Innovator Ranibizumab molecule, Lane 3: -, Lane 4: *E. coli* SHuffle® T7 (DE3) supernatant, Lane 5: *E. coli* SHuffle® T7 Express (DE3) supernatant.

Western blotting of the partially purified cell lysate supernatant obtained from both the microbial strains was performed to confirm the presence of in-vivo refolded rHu Ranibizumab antibody fragment. The samples along with a protein marker and standard were allowed to run on a 12% SDS-PAGE gel as mentioned above and then used for blotting onto a nitrocellulose membrane. Post blotting, the membrane was subjected to blocking in a blocking buffer containing 5% skim milk in PBST buffer at 4° C. overnight. Post-overnight incubation, the purified primary antibody was used at a dilution of 1:1000 in the blocking buffer and kept for incubation at 4° C. for three hours. The membrane was washed with PBST buffer (3 times) and subjected to incubation with Goat Anti-Rabbit IgG (H+L), HRP conjugated in the blocking buffer at 4° C. for one hour. Following this, the membrane was washed with PBST buffer (3 times) and treated with staining solution containing 0.5 mg/mL DAB (Diaminobenzene), 50% hydrogen peroxide and metal enhancers namely; nickel ammonium sulphate and cobalt chloride in PBS buffer. FIG. 6(a) shows western blot of innovator Ranibizumab molecule and partially purified in-vivo refolded rHu Ranibizumab expressed in Shuffle T7 (DE3) and Shuffle T7 Express (DE3).

(iv) Reverse Phase HPLC Analysis of rHu Ranibizumab

Figure 7A:
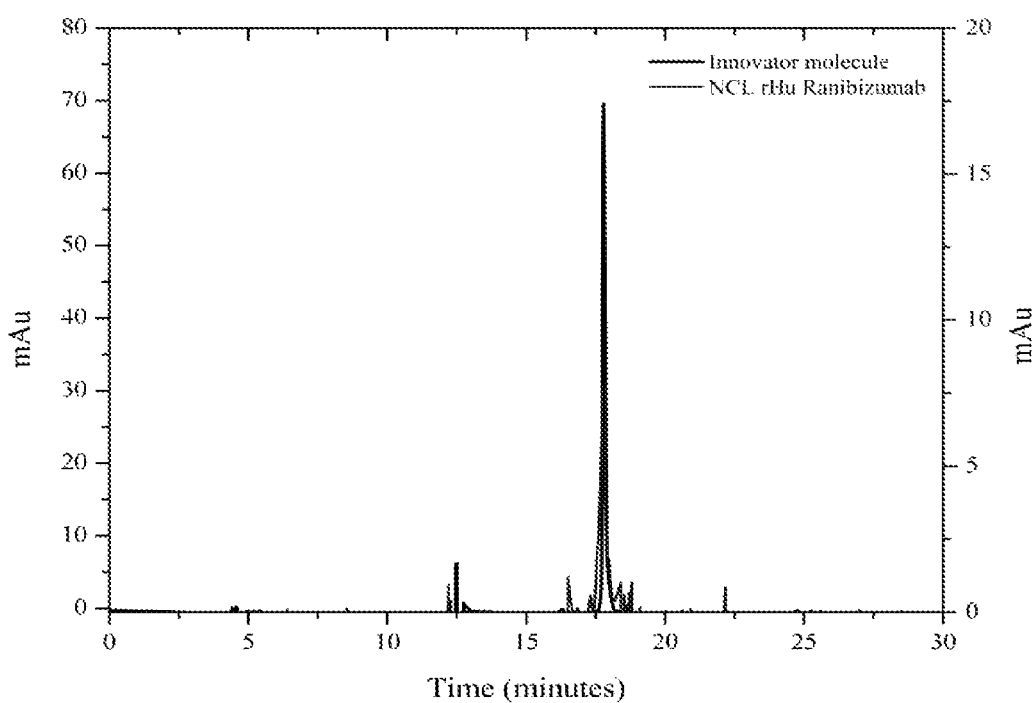
FIG. 7 depicts RP-HPLC analysis overlay of in-vivo refolded biosimilar rHu Ranibizumab in a shake flask culture system and Innovator Ranibizumab molecule, in FIG. 7(a) and RP-HPLC analysis overlay of in-vivo refolded biosimilar rHu Ranibizumab obtained in bioreactor in FIG. 7(b).

Quantitative and qualitative analysis of in-vivo refolded rHu Ranibizumab was performed using Reversed Phase High-Performance Liquid Chromatography (RP-HPLC) analysis. RP-HPLC analysis was carried out with a 4.6 mm×250 mm Aeris™ 3.6 µm WIDEPORE XB-C8 column (Phenomenex, USA) operated with Agilent 1200 HPLC system. RP-HPLC data was recorded and analyzed using Agilent ChemStation software. Mobile phase consisted of 0.1% (v/v) TFA in water (solvent A) and 0.1% (v/v) TFA, 70% (v/v) of acetonitrile and 20% (v/v) of isopropyl alcohol (solvent B). The flow rate was maintained at 0.5 ml/min using a linear gradient of A to B at a wavelength of 280 nm. FIG. 7(a) shows RP-HPLC chromatogram of innovator Ranibizumab and in-vivo refolded rHu Ranibizumab.

(v) Intact Mass Analysis of In-Vivo Refolded rHu Ranibizumab by Matrix-Assisted Laser Desorption/Ionization (MALDI-TOF) (Time-of-Flight Mass Spectrometer)

Figure 8A:
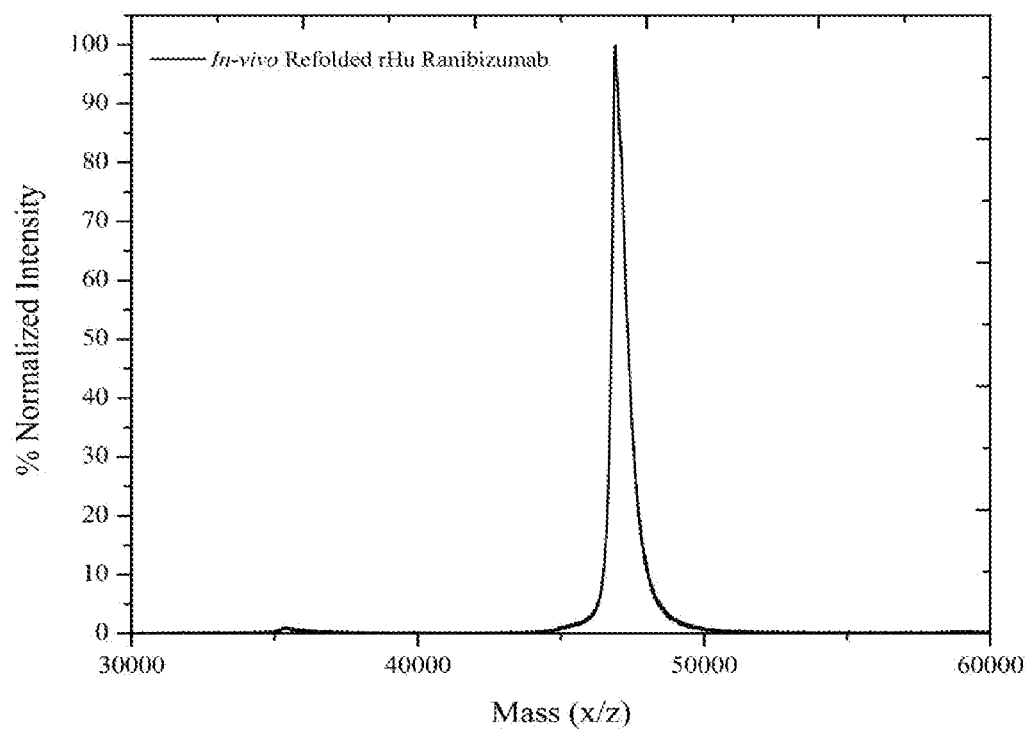
FIG. 8 depicts intact mass analysis of in-vivo refolded biosimilar rHu Ranibizumab obtained in shake flask culture system in FIG. 8(a) and an overlay of purified in-vivo refolded rHu biosimilar Ranibizumab with the Innovator Ranibizumab molecule under non-reducing conditions using MALDI-TOF MS in FIG. 8(b) in a bioreactor scale.
Figure 8B:
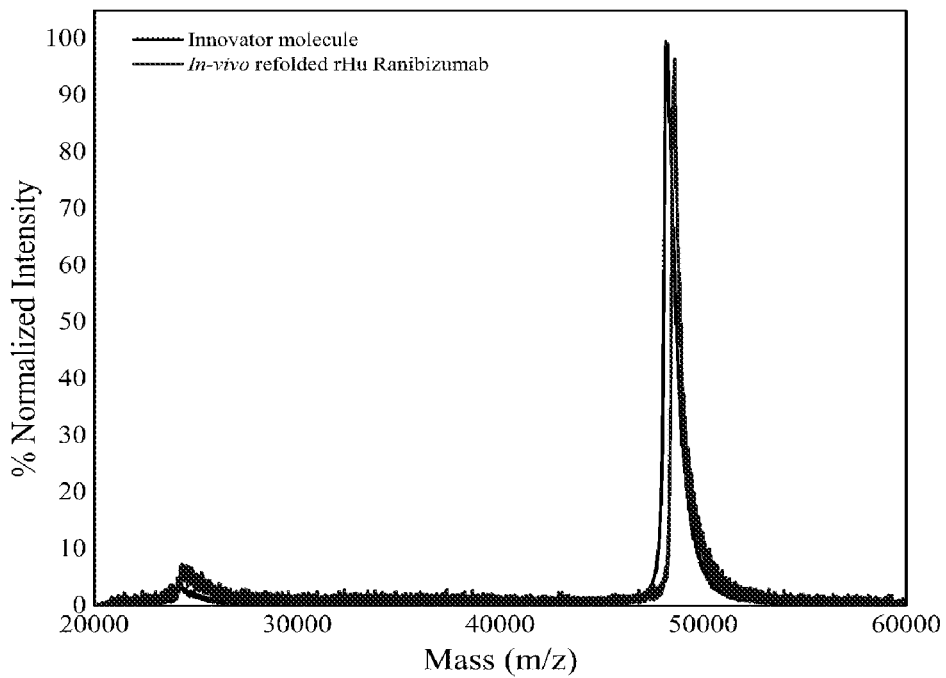

In-vivo refolded purified rHu Ranibizumab was mixed with sinapinic acid matrix in a 1:1 ratio to perform MALDI-TOF analysis (FIG. 8(a)). Matrix sinapinic acid (20 mg/ml) was prepared in 50% v/v acetonitrile, 0.1% v/v TFA in high purity water. 1 µl of the homogenized mixture of sample and matrix was deposited on a clean 384 well MALDI plate. The plate was inserted into AB SCIEX TOF/TOF™ 5800 instrument and the instrument was used in the linear positive ion mode. Nitrogen laser at 337 nm radiation was kept as an ionization source. Laser intensity in between 5000 to 6000 was used for the analysis of samples. Result analysis was performed using Data Explorer® Software Version 4.11.

Example 5

Growth Kinetics of Transformed Shuffle® T7 (DE3) and Shuffle® T7 Express (DE3) in Chemically Defined Minimal Media and Modified Complex Media The growth characteristics of two redox mutant strains were studied in chemically defined minimal media with composition: 4 g/L $(NH_4)_2HPO_4$, 13.3 g/L $KH_2PO_4$, 1.7 g/L citric acid and 31.5 g/L glycerol, pH 6.8. The partial media was sterilized for 15 minutes at 121° C. Trace elements (2.5 ml/L) consisting of EDTA (8.4 mg/L), thiamine hydrochloride (10 mg/L) and $MgSO_4$ (1.2 g/L) were separately dissolved in autoclaved water, filtered by 0.22µ syringe filter and directly added to flasks. Composition of trace elements per liter was as follows: $CoCl_2·6H_2O$ (2.5 mg), $MnCl_2·4H_2O$ (15.0 mg), $CuCl_2 \cdot 2H_2O$ (1.5 mg), $H_3BO_3$ (3.0 mg), $Na_2MoO_4 \cdot 2H_2O$ (2.5 mg), $Zn(CH_3COO)_2 \cdot 2H_2O$ (13.0 mg) and Fe (III) citrate (100 mg). For the growth of SHuffle® T7 (DE3) *E. coli*, leucine and isoleucine to a final concentration of 50 μg/ml were added to chemically defined media in culture flasks as it is an auxotroph for these amino acids. FIGS. 9 and 10 show growth characteristics of the two redox mutant strains in chemically defined minimal media and modified complex media respectively.

Example 6

Optimization of Process Parameters Based on a DoE Approach

Response surface methodology (RSM) using Box-Behnken design was used to optimize and understand the impact of various processing parameters like pre-induction optical density, post-induction temperature and inducer concentration on quantity and quality of in-vivo refolded recombinant rHu Ranibizumab. The experiments were formulated using JMP software. All the shake flask experiments were conducted in duplicates using chemically defined minimal media and protein yield was calculated using RP-HPLC analysis. Three different parameters were selected as follows:

Pre-induction O.D. (Strain-dependent): Early-log, Mid-log and Late-log phase.
Post-induction temperature: 10° C., 16° C. and 22° C.
Inducer concentration: 0.1 mM, 0.55 mM and 1 mM IPTG.

A total of 30 experimental trials including 16 trials for factorial design, eight trials for axial points and six trials for replication of the central points were performed.

TABLE 1

Box-Behnken design for optimization of various process parameters impacting expression levels of in-vivo refolded recombinant Ranibizumab in SHuffle ® T7 (DE3)

| Post-induction temperature | Pre-induction optical density | Inducer concentration (mM) | In-vivo Refolded rHu Ranibizumab expression (mg/L) |
|---|---|---|---|
| 16 | Mid-log | 0.55 | 40.34 |
| 16 | Early-log | 0.1 | 21.21 |
| 16 | Late-log | 0.1 | 25.65 |
| 16 | Early-log | 1 | 13.31 |
| 16 | Late-log | 1 | 26.60 |
| 22 | Mid-log | 0.1 | 50.82 |
| 22 | Early-log | 0.55 | 17.18 |
| 22 | Late-log | 0.55 | 43.06 |

TABLE 1-continued

Box-Behnken design for optimization of various process parameters impacting expression levels of in-vivo refolded recombinant Ranibizumab in SHuffle ® T7 (DE3)

| Post-induction temperature | Pre-induction optical density | Inducer concentration (mM) | In-vivo Refolded rHu Ranibizumab expression (mg/L) |
|---|---|---|---|
| 22 | Mid-log | 1 | 45.26 |
| 10 | Mid-log | 1 | 38.31 |
| 10 | Mid-log | 0.1 | 31.41 |
| 10 | Early-log | 0.55 | 18.21 |
| 10 | Late-log | 0.55 | 53.55 |

TABLE 2

Box-Behnken design for optimization of various process parameters impacting expression levels of in-vivo refolded Ranibizumab in SHuffle ® T7 Express (DE3)

| Post-induction temperature | Pre-induction optical density | Inducer concentration (mM) | In-vivo Refolded rHu Ranibizumab expression (mg/L) |
|---|---|---|---|
| 16 | Mid-log | 0.55 | 26.87 |
| 16 | Late-log | 0.1 | 13.63 |
| 16 | Early-log | 0.1 | 15.63 |
| 16 | Late-log | 1 | 14.15 |
| 16 | Early-log | 1 | 14.90 |
| 22 | Mid-log | 0.1 | 11.95 |
| 22 | Mid-log | 0.1 | 12.55 |
| 22 | Early-log | 0.55 | 7.00 |
| 22 | Late-log | 0.55 | 8.88 |
| 10 | Mid-log | 0.1 | 18.20 |
| 10 | Late-log | 0.55 | 16.80 |
| 10 | Mid-log | 1 | 15.13 |
| 10 | Early-log | 0.55 | 9.41 |

Example 7

Impact of Media Composition on In-Vivo Refolded rHu Ranibizumab Expression

The optimal conditions for high expression levels of in-vivo refolded rHu Ranibizumab were identified based on statistical analysis using JMP software. The effect of media composition on soluble protein expression levels was studied using a modified complex media consisting of 47.6 g/L Tartoff Hobbs HiVeg Terrific broth and 31.5 g/L of glycerol. About 1.5 to 2 folds increase in in-vivo refolded rHu Ranibizumab expression levels was observed in the modified complex media as compared to chemically defined minimal media (Table 3).

TABLE 3

In-vivo Refolded rHu Ranibizumab expression levels under optimal process conditions in modified complex media and chemically defined minimal media

| Strain | Media | Post-induction temperature | Pre-induction O.D.$_{600}$ | Inducer conc. (mM) | In-vivo Refolded rHu Ranibizumab expression (mg/L) |
|---|---|---|---|---|---|
| SHuffle ® T7 (DE3) | Defined | 22 | Mid-log | 0.55 | 50.82 ± 2.92 |
| | Complex | 22 | Mid-log | 0.55 | 85.25 ± 5.71 |
| SHuffle ® T7 Express (DE3) | Defined | 16 | Mid-log | 0.55 | 23.71 ± 0.82 |
| | Complex | 16 | Mid-log | 0.55 | 56.28 ± 2.96 |

Example 8

Production of In-Vivo Refolded Recombinant Humanized Ranibizumab at the Bioreactor Scale The optimal conditions identified at the shake flask scale were replicated at the bioreactor scale using modified complex media in a batch mode for both *E. coli* SHuffle T7 (DE3) and SHuffle T7 Express (DE3) strains. Bioreactor scale cultivations were carried out at 30° C. in a two litre reactor (one litre working volume). 100 ml of 4 hours old seed culture (secondary culture) was used to inoculate 900 ml of media in the bioreactor. The bioreactor assembly consisted of two Rushton impellers, a ring sparger (macro sparger) and was outfitted with an external refrigerated/heating circulator to maintain the reactor temperature. Initial culture conditions were as follows: one litre initial culture volume, 0.5 vvm air flow rate, agitation at 300 rpm, pH ~7.0. The dissolved oxygen (DO) was maintained at 30% of air saturation using an agitation cascade from 300 to 1000 rpm and $O_2$ enrichment from 0 to 90%. The pH was controlled at ~7.0 by addition of 15% v/v aqueous ammonia and 30% v/v orthophosphoric acid. Foaming in the bioreactor was controlled by addition of 20% v/v antifoam reagent. When the bacterial culture reached an optical density of about ~20.0 to 25.0 i.e. mid-log phase, the temperature was reduced to 22° C. for SHuffle T7 (DE3) and 16° C. for SHuffle T7 Express (DE3) and the culture was induced using 0.55 mM IPTG. Samples were aseptically withdrawn from the bioreactor at regular time intervals for optical density (600 nm) and Dry Cell Weight (DCW) measurements. Gram staining was performed to ensure there was no contamination in the developed protocol.

Example 10

Cell Lysis and Post-Harvest Processing

The cell biomass was obtained by centrifuging the culture broth at 6000 rpm, 10° C. for 30 minutes. The pellet obtained was dissolved in 50 ml lysis buffer (100 mM Tris, 50 mM NaCl, 5 mM EDTA). A high-pressure homogenizer was used for mechanical cell disruption at 15,000 psi for 7 minutes. Post cell lysis, the cell lysate obtained was subjected to centrifugation at 6000 rpm, 10° C. for 30 minutes. The supernatant fraction obtained was collected and used for purification of in-vivo refolded rHu Ranibizumab.

Example 11

Purification of In-Vivo Refolded rHu Ranibizumab

The use of fusion partners with biotherapeutic proteins and clearance of the same from the final drug product is potentially of concern to food and drug regulatory authorities. To comply with the same, the use of fusion partners/affinity tags was avoided in this investigation and the purification of the in-vivo refolded rHu Ranibizumab expressed in the soluble fraction was performed using a combination of precipitation and chromatography steps.

(a) Isoelectric Point Based Precipitation

Figure 5A:
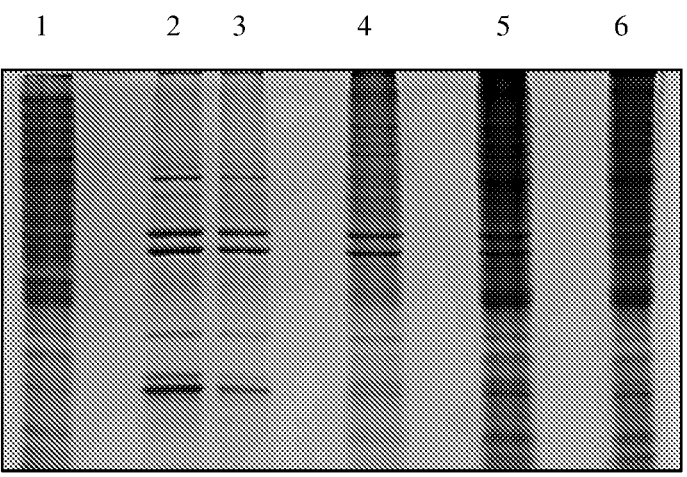
FIG. 5(a): Lane 1: Crude cell lysate supernatant in wherein Lane 2: pH 7.5; Lane 3: pH 7.0; Lane 4: pH 6.0; Lane 5: pH 5.0; Lane 6: pH 4.0.
Figure 5B:
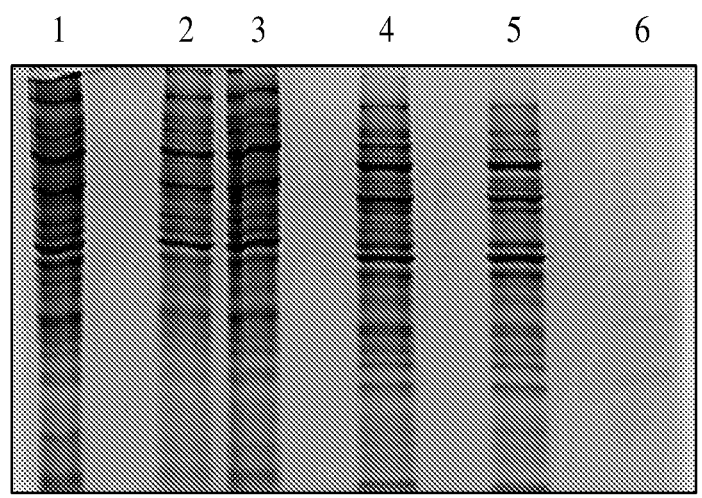
FIG. 5(b) depicts the SDS-PAGE analysis of the supernatant obtained post isoelectric point based precipitation. Lane 1: Crude cell lysate supernatant; Lane 2: pH 7.5; Lane 3: pH 7.0; Lane 4: pH 6.0; Lane 5: pH 5.0; Lane 6: pH 4.0.

Isoelectric point based precipitation of host cell proteins was carried out at pH 4.0, 5.0, 6.0, 7.0 and 7.5. The cell free supernatant obtained post lysis was subjected to isoelectric point based precipitation using 50% glacial acetic acid and stirring for about 60 minutes. Post precipitation, the resultant fraction was subjected to centrifugation at 6500 rpm, 10° C. for 20 minutes. Maximum precipitation of *E. coli* host cell proteins was observed at pH 4.0 as compared to pH 5.0, 6.0, 7.0 and 7.5 (FIGS. 5a and 5b). Based on these results, all subsequent downstream process development was carried out by subjecting the supernatant obtained post cell lysis to precipitation at pH 4.0. The supernatant obtained post precipitation and centrifugation was subjected to ultrafiltration and in-vivo refolded rHu Ranibizumab was collected majorly in the retentate fraction with negligible amounts of in-vivo refolded rHu Ranibizumab being lost in the wash fraction as confirmed by RP-HPLC analysis.

(b) Ultrafiltration

Following isoelectric point based precipitation, the supernatant was subjected to ultrafiltration using Ultrasette™ lab tangential flow filtration device with a molecular weight cut-off of ~ 5 kDa into a 20 mM Tris pH 9.0 equilibration buffer. The retentate further obtained through ultrafiltration was subjected to purification based on a dual strategy i.e. a combination of multimodal and affinity chromatography.

(c) Multimodal Chromatography

Figure 13:
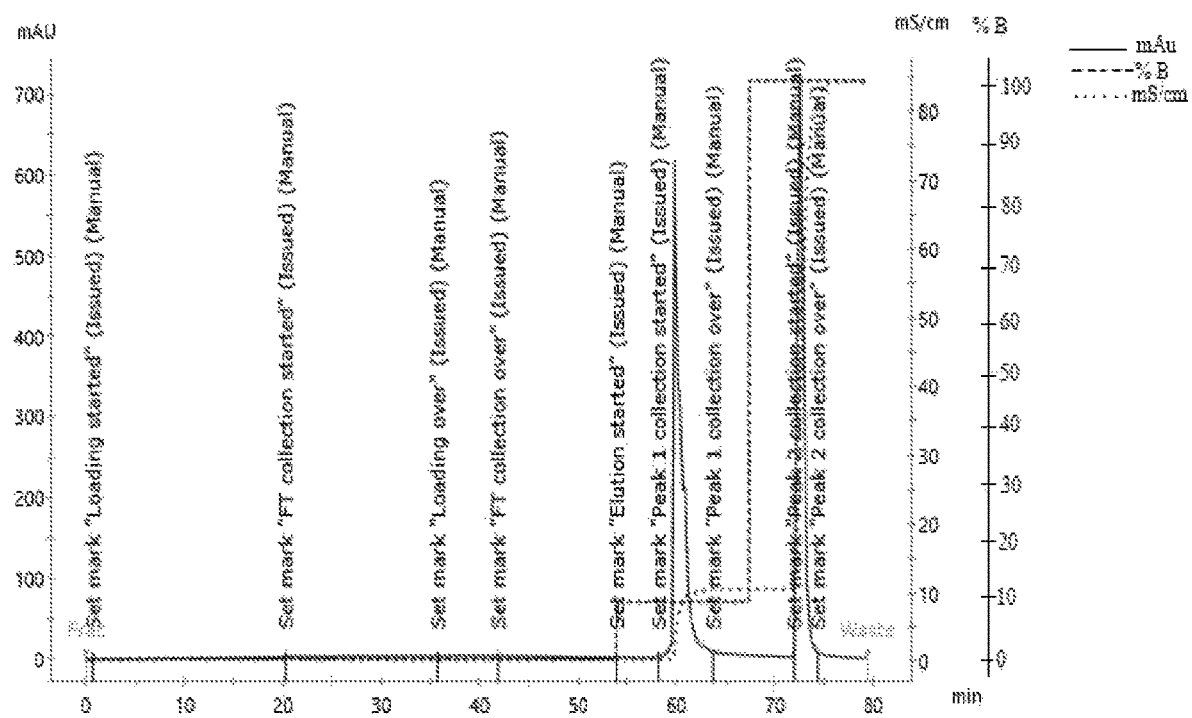
FIG. 13 depicts a chromatogram for purification of in-vivo refolded rHu Ranibizumab (Step 1) using a multimodal chromatography.

Cell-free supernatant obtained post ultrafiltration was buffer exchanged into the aforementioned equilibration buffer using a XK-26™ (GE Healthcare, US) chromatography column (26×1000 mm) packed with 28.0±0.5 cm HiTrap Desalting Sephadex G-25 resin (GE Healthcare, USA). Omnifit™ (Diba industries, UK) chromatography column (6.6×450 mm) was used to pack 15.0±0.2 cm BAKER BOND™ XWP 500 Poly PEI-35 multimodal resin. The chromatography column was equilibrated using the selected equilibration buffer i.e. 20 mM Tris pH 9.0 (5-10 CV). The buffer exchanged output was then injected into the chromatography column using a sample pump. After sample loading, the unbound protein sample was removed using equilibration buffer wash step (5 CV). Elution step consisted of selective salt based elution gradient involving a step gradient of 10% elution buffer followed by a step gradient to 100% of elution buffer. The output from the chromatography column was monitored using pH, conductivity and UV detection at 280, 260 and 215 nm. FIG. 13 shows chromatogram for multimodal chromatography operation (step 1). Elute obtained in the 10% gradient elution step was then used for loading onto the affinity column.

(d) Affinity Chromatography

Figure 14:
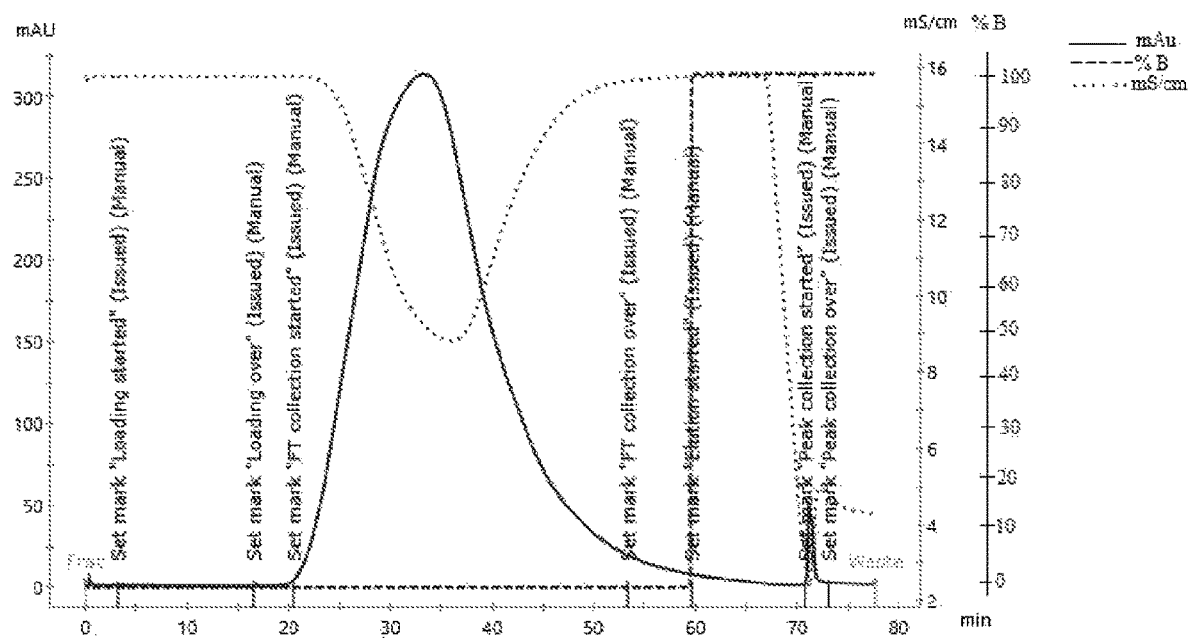
FIG. 14 depicts a chromatogram for purification of in-vivo refolded rHu Ranibizumab (Step 2) using an affinity chromatography.

Omnifit™ chromatography column (6.6×450 mm) was used to pack 13.3±0.1 cm CH1-XL™ affinity resin (affinity for the heavy chain of antibody fragments). The chromatography column was equilibrated using 1× phosphate buffer saline pH 7.2 (5-10 CV). The output obtained from the first step gradient (10%) in the multimodal chromatography step was injected into this chromatography column using a sample pump. Post sample loading, the unbound protein sample was allowed to flow through using an equilibration buffer wash step (5-7 CV). Elution step consisted of a selective pH based step gradient to 100% of the elution buffer i.e. 100 mM Glycine-HCl pH 2.5. The output obtained post elution was buffer exchanged into 10 mM Acetate buffer pH 5.5. FIG. 14 shows the chromatogram for affinity chromatography operation (step 2). Purification using the CH1-XL affinity matrix was performed in a bind and elute mode through binding at a higher pH and elution at a lower pH resulting in a final purity of 99.44%.

Example 12

Analytical Assay Development for Characterization of In-Vivo Refolded Biosimilar rHu Ranibizumab Various orthogonal analytical assays (RP-HPLC, SDS-PAGE, Western Blotting and MALDI-TOF MS) were performed for the characterization of in-vivo refolded and purified biosimilar rHu Ranibizumab.

(a) SDS-PAGE Analysis

SDS-PAGE analysis for characterization of in-vivo refolded rHu Ranibizumab expressed using the two strains was carried out using 12% (Thickness 1 mm) of the resolving gel under non-reducing conditions at the stacking gel constant voltage 100V and resolving gel constant voltage 80V conditions. Each sample was boiled for 10 minutes in the starting buffer before being loaded onto the gel. 0.05% (w/v) Coomassie brilliant blue G-250 in 4:1:5 (Water:Glacial Acetic acid:Methanol) was used to detect proteins after electrophoretic separation on polyacrylamide gels. In-vivo refolded rHu Ranibizumab expressed using the redox mutant E. coli strains was characterized using various orthogonal analytical assays. The purified in-vivo refolded antibody fragment was analyzed using SDS-PAGE under non-reduced conditions and detected by Coomassie blue staining. The in-vivo refolded rHu Ranibizumab migrated with an expected mobility of ~48 kDa identical to that of innovator Ranibizumab molecule (FIG. 4(c)).

(b) Western Blot Analysis

Western blotting of the purified protein obtained from both the strains was performed to confirm the presence of in-vivo refolded rHu Ranibizumab antibody fragment. The samples along with a protein marker and standard were allowed to run on a 12% SDS-PAGE gel as mentioned above and then used for blotting onto a nitrocellulose membrane. Post blotting, the membrane was subjected to blocking in a blocking buffer containing 5% skim milk in PBST (1×PBS'0.1% Tween-20) buffer at 4° C. overnight. Post-overnight incubation, the purified primary antibody was used at a dilution of 1:1000 in the blocking buffer and kept for incubation at 4° C. for three hours. The membrane was washed with PBST buffer (3 times) and subjected to incubation with Goat Anti-Rabbit IgG (H+L), HRP conjugated in the blocking buffer at 4° C. for one hour. Following this, the membrane was washed with PBST buffer (3 times) and subjected to the staining solution containing 0.5 mg/mL DAB (Diaminobenzene), 50% hydrogen peroxide and metal enhancers namely; nickel ammonium sulphate and cobalt chloride in PBS buffer.

Figure 6B:
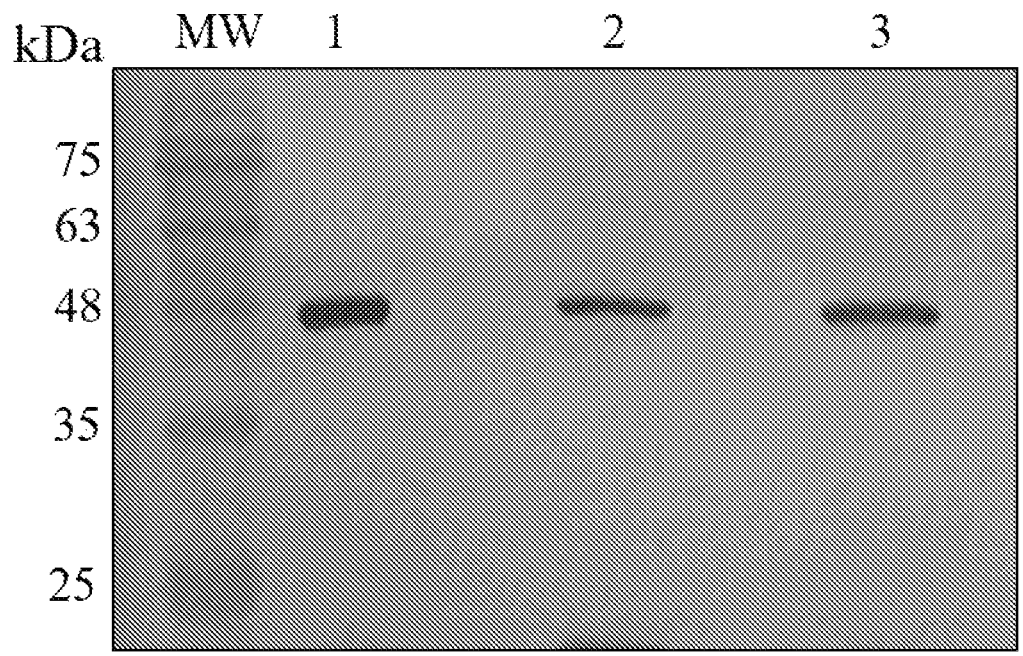
FIG. 6(b) depicts the Western blot analysis of in-vivo refolded rHu Ranibizumab antibody fragment under non-reducing conditions; Lane MW: Standard molecular weight marker, Lane1: Innovator Ranibizumab molecule, Lane 2: Purified refolded protein expressed using *E. coli* SHuffle T7 (DE3), Lane 3: Purified refolded protein expressed using *E. coli* SHuffleT7 Express (DE3).

Western blotting analysis was used to confirm that the protein purified using the developed purification protocol is the protein of interest i.e. in-vivo refolded rHu Ranibizumab. The purified protein was detected at ~ 48 kDa identical to that of the innovator Ranibizumab molecule (FIG. 6(b)). It is important to note that the primary antibody used for the western blotting protocol was raised specifically against rHu Ranibizumab and therefore the possibility of detecting any false positives is minimised.

(c) Reverse Phase HPLC Analysis

Quantitative and qualitative analysis of in-vivo refolded rHu Ranibizumab was performed using Reversed Phase High-Performance Liquid Chromatography (RP-HPLC) analysis. RP-HPLC analysis was carried out with a 4.6 mm×250 mm Aeris™ 3.6 µm WIDEPORE XB-C8 column (Phenomenex, USA). The mobile phase consisted of 0.1% (v/v) TFA in water (solvent A) and 0.1% (v/v) TFA, 70% (v/v) of acetonitrile and 20% (v/v) of isopropyl alcohol (solvent B). The flow rate was maintained at 0.5 ml/min using a linear gradient of A to B at a wavelength of 280 nm.

Figure 7B:
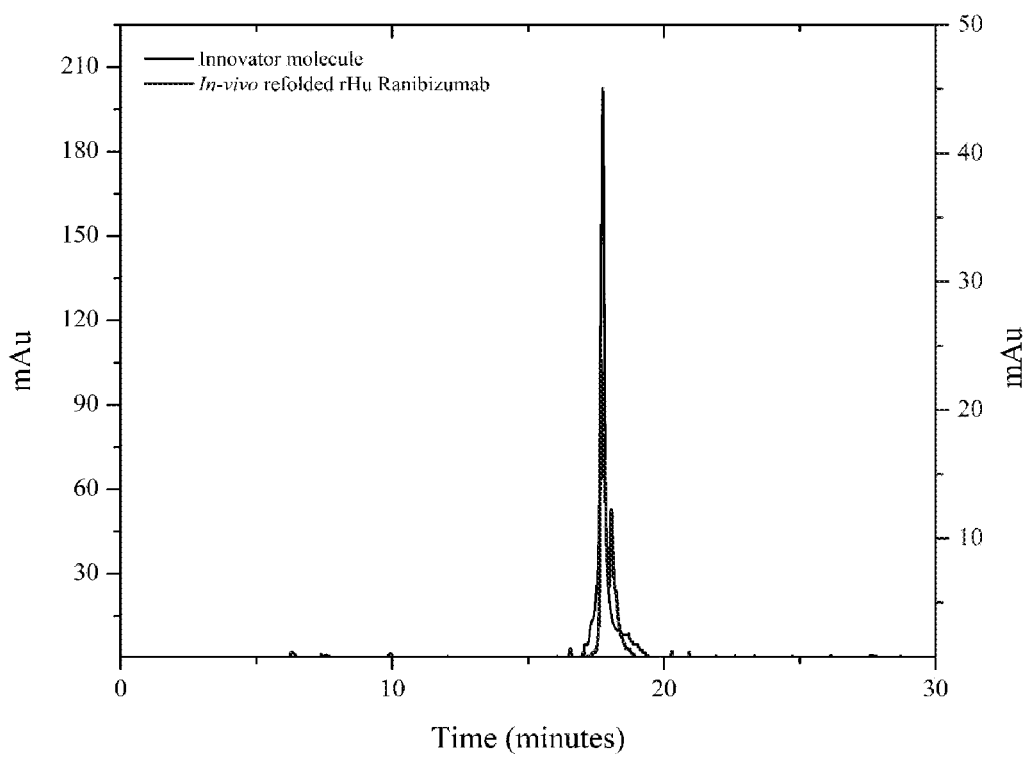

RP-HPLC analysis of the purified and in-vivo refolded rHu Ranibizumab antibody fragment under non-reduced conditions shows conformity with the innovator Ranibizumab molecule Lucentis (Genentech Inc., USA) (FIG. 7(b)).

(d) Intact Mass Analysis Using Matrix-Assisted Laser Desorption/Ionization (MALDI-TOF) (Time-of-Flight Mass Spectrometer)

Standard and purified in-vivo refolded rHu Ranibizumab with sinapinic acid matrix were mixed in 1:1 ratio to perform MALDI-TOF MS analysis. Matrix sinapinic acid (20 mg/ml) was prepared in 50% v/v acetonitrile, 0.1% v/v TFA in high purity water. 1 µl of the homogenized mixture of sample and matrix was deposited on a clean 384 well MALDI plate. The plate was inserted into AB SCIEX TOF/TOF™ 5800 instrument and the instrument was used in the linear positive ion mode. Nitrogen laser at 337 nm radiation was kept as an ionization source. Laser intensity in between 5000 to 6000 was used for the analysis of samples. MALDI-TOF MS analysis of purified in-vivo refolded rHu Ranibizumab antibody fragment under non-reduced conditions confirmed the intact mass of ~48 kDa identical to that of the innovator Ranibizumab molecule (FIG. 8(b)).

TABLE 4

Comparative data between the process for producing in-vitro refolded recombinant humanized Ranibizumab disclosed in Indian Patent Application No. 201711017654 and the process for producing in-vivo refolded recombinant humanized Ranibizumab in the present application

| | Indian Patent Application No. 201711017654 | Present Application |
|---|---|---|
| Process time requirements: Upstream and refolding | 9 days | 3 days |
| Process yield | 30.00 ± 5.00% | 45 ± 5.00% |
| Cost reduction | NA | 30.0 % cost reduction due to removal of in-vitro refolding |

We claim:

1. A process for expression and recovery of an in-vivo refolded recombinant antibody fragment in a soluble form comprising:
   a) providing a microbial host cell overexpressing disulfide isomerase and lacking expression of enzymes that promote a reducing ability of cytoplasm, said cell comprising a DNA construct encoding light and heavy chain of a recombinant antibody fragment;
   b) culturing said microbial host cell of step (a) in a complex nutrient medium comprising glycerol at 30° C., pH 7 to obtain a culture;
   c) reducing temperature of the culture and adding IPTG to said culture to induce expression to obtain a culture broth comprising in-vivo refolded recombinant antibody fragment;
   d) centrifuging the culture broth of step (c) to obtain a cell mass;
   e) disrupting the cell mass of step (d) to obtain a cell lysate;
   f) centrifuging the cell lysate of step (e) to obtain a first supernatant;
   g) precipitating the first supernatant of step (f) at pH 4.0 followed by centrifugation to obtain a second supernatant;
   h) subjecting the second supernatant of step (g) to ultrafiltration to obtain the in-vivo refolded recombinant antibody fragment in a retentate fraction;
   i) subjecting said retentate fraction of step (h) to a multimodal chromatography and an affinity chromatography to obtain the purified in-vivo refolded recombinant antibody fragment in a soluble form.

2. The process as claimed in claim 1, wherein the recombinant antibody fragment is a fragment of recombinant Human Ranibizumab.

3. The process as claimed in claim 1, wherein the microbial host cell is an *E. coli* host cell.

4. The process as claimed in claim 3, wherein the *E. coli* host cell is selected from the group consisting of SHuffle T7 and SHuffle T7 Express cells.

5. The process as claimed in claim 1, wherein in step (c), the temperature of the culture is reduced from 30° C. to a temperature in the range of 15° C. to 24° C. during induction.

6. The process as claimed in claim 1, wherein IPTG is added at a concentration in a range of 0.55 mM to 1 mM.

7. The process as claimed in claim 1, wherein the process is performed with dissolved oxygen (DO) at a concentration of 30% of air saturation with agitation in a range of 300 to 1000 rpm and $O_2$ enrichment from 0 to 90%.

8. The process as claimed in claim 1, wherein the culture is induced at an optical density in a range of about 20.0 to 25.0 in mid-log phase growth phase.

9. The process as claimed in claim 1, wherein the glycerol concentration in the complex nutrient medium is in the range of 30 g/L to 35 g/L.

10. The process as claimed in claim 1, wherein the affinity chromatography is performed in a bind and elute mode with binding at a pH range of 8.5 to 10.5 and elution at a pH range of 2.5 to 4.5.

11. A process for expression and recovery of an in-vivo refolded recombinant antibody fragment in a soluble form comprising:
    a) providing a microbial host cell overexpressing disulfide isomerase and lacking expression of enzymes that promote a reducing ability of cytoplasm, said cell comprising a DNA construct encoding light and heavy chain of a recombinant antibody fragment;
    b) culturing said microbial host cell of step (a) in a complex nutrient medium comprising glycerol at 30° C., pH 7 to obtain a culture;
    c) reducing temperature of the culture and adding IPTG to said culture to induce expression to obtain a culture broth comprising in-vivo refolded recombinant antibody fragment, wherein the culture is induced at an optical density in a range of about 20.0 to 25.0;
    d) centrifuging the culture broth of step (c) to obtain a cell mass;
    e) disrupting the cell mass of step (d) to obtain a cell lysate;
    f) centrifuging the cell lysate of step (e) to obtain a first supernatant;
    g) precipitating the first supernatant of step (f) at pH 4.0 followed by centrifugation to obtain a second supernatant;
    h) subjecting the second supernatant of step (g) to ultrafiltration to obtain the in-vivo refolded recombinant antibody fragment in a retentate fraction; and
    i) subjecting said retentate fraction of step (h) to a multimodal chromatography and an affinity chromatography to obtain the purified in-vivo refolded recombinant antibody fragment in a soluble form.

\* \* \* \* \*

SEQUENCE LISTING

```
<160> NUMBER OF SEQ ID NOS: 4

<210> SEQ ID NO 1
<211> LENGTH: 721
<212> TYPE: DNA
<213> ORGANISM: Artificial sequence
<220> FEATURE:
<223> OTHER INFORMATION: DNA

<400> SEQUENCE: 1
gagctcatat ggaagttcag ctggttgaaa gcggtggtgg tctggttcag cctggtggta        60
gcctgcgtct gagctgtgca gcaagcggtt atgattttac ccattatggt atgaattggg       120
```

```
ttcgtcaggc accgggtaaa ggtctggaat gggttggttg gattaatacc tataccggtg    180
aaccgaccta tgcagcagat tttaaacgtc gttttacctt tagcctggat accagcaaaa    240
gcaccgcata tctgcagatg aatagcctgc gtgcagagga taccgcagtg tattattgtg    300
caaaatatcc gtattattac ggcaccagcc attggtattt cgatgtttgg ggtcagggca    360
ccctggttac cgttagcagc gcaagcacca aaggtccgag cgttttccg ctggcaccga    420 gcagcaaaag taccagcggt ggcaccgcag cactgggttg tctggttaaa gattattttc    480
cggaaccggt taccgtgagc tggaatagcg gtgcactgac cagcggtgtt cataccttc    540 cggcagttct gcagagcagc ggtctgtata gcctgagcag cgttgttacc gttccgagca    600
gcagcctggg cacccagacc tatatttgta atgttaatca taaaccgagc aataccaaag    660
tggataaaaa agtggaaccg aaaagctgcg ataaaaccca tctgtaatag ctcgagccgc    720
g    721
```

<210> SEQ ID NO 2
<211> LENGTH: 231
<212> TYPE: PRT
<213> ORGANISM: Artificial sequence
<220> FEATURE:
<223> OTHER INFORMATION: Polypeptide sequence of heavy chain of Ranibizumab

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Leu
225                 230
```

<210> SEQ ID NO 3
<211> LENGTH: 669
<212> TYPE: DNA
<213> ORGANISM: Artificial sequence
<220> FEATURE:
<223> OTHER INFORMATION: DNA

<400> SEQUENCE: 3

```
gagctccatg gatattcagc tgacccagag cccgagcagc ctgagcgcaa gcgttggtga    60
tcgtgttacc attacctgta gcgcaagcca ggatattagc aattatctga attggtatca   120
gcagaaaccg ggtaaagcac cgaaagtgct gatctatttt accagcagcc tgcatagcgg   180
tgttccgagc cgttttagcg gtagcggtag tggcaccgat tttaccctga ccattagcag   240
cctgcagccg aagattttg caacctatta ttgtcagcag tatagcaccg ttccgtggac   300
ctttggtcag ggcaccaaag ttgaaattaa acgtaccgtt gcagcaccga gcgtttttat   360
ctttccgcct agtgatgaac agctgaaaag cggcaccgca agcgttgttt gtctgctgaa   420
taacttttat ccgcgtgaag caaaagttca gtggaaagtt gataatgcac tgcagagcgg   480
taatagccaa gaaagcgtta ccgaacagga tagcaaagat agcacctata gcctgagcag   540
caccctgacc ctgagcaaag cagattatga aaaacacaaa gtgtatgcct gcgaagttac   600
ccatcagggt ctgagcagtc cggttaccaa aagtttaat cgtggtgaat gctaatagaa   660
gcttggtac                                                           669
```

<210> SEQ ID NO 4
<211> LENGTH: 214
<212> TYPE: PRT
<213> ORGANISM: Artificial sequence
<220> FEATURE:
<223> OTHER INFORMATION: Polypeptide sequence of Light chain of
      Ranibizumab

<400> SEQUENCE: 4

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210
```